(12) United States Patent
Kobayashi et al.

(10) Patent No.: US 9,273,130 B2
(45) Date of Patent: Mar. 1, 2016

(54) PHARMACEUTICAL COMPOSITION FOR TREATMENT AND/OR PREVENTION OF CANCER

(71) Applicant: TORAY INDUSTRIES, INC., Tokyo (JP)

(72) Inventors: Shinichi Kobayashi, Kamakura (JP); Fumiyoshi Okano, Kamakura (JP); Takanori Saito, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/379,876

(22) PCT Filed: Feb. 21, 2013

(86) PCT No.: PCT/JP2013/054337
§ 371 (c)(1),
(2) Date: Aug. 20, 2014

(87) PCT Pub. No.: WO2013/125636
PCT Pub. Date: Aug. 29, 2013

(65) Prior Publication Data
US 2015/0004171 A1    Jan. 1, 2015

(30) Foreign Application Priority Data

Feb. 21, 2012 (JP) ................................ 2012-035484

(51) Int. Cl.
| *C07K 16/30* | (2006.01) |
| *A61K 39/395* | (2006.01) |
| *C07K 16/18* | (2006.01) |
| *C07K 16/28* | (2006.01) |
| *A61K 39/00* | (2006.01) |

(52) U.S. Cl.
CPC ............. *C07K 16/18* (2013.01); *A61K 39/3955* (2013.01); *C07K 16/28* (2013.01); *C07K 16/30* (2013.01); *A61K 2039/505* (2013.01); *C07K 2317/24* (2013.01); *C07K 2317/34* (2013.01); *C07K 2317/732* (2013.01)

(58) Field of Classification Search
CPC .............. C07K 16/30; C07K 16/315–16/3069; C07K 16/461–16/467; A61K 39/395; A61K 39/39558
See application file for complete search history.

(56) References Cited

U.S. PATENT DOCUMENTS

| 5,698,396 | A | 12/1997 | Pfreundschuh |
| 6,335,170 | B1 | 1/2002 | Orntoft |
| 6,444,425 | B1 | 9/2002 | Reed et al. |
| 7,449,184 | B2 | 11/2008 | Allison et al. |
| 7,485,302 | B2 | 2/2009 | Adams et al. |
| 7,745,391 | B2 | 6/2010 | Mintz et al. |
| 8,008,431 | B2 | 8/2011 | Weinschenk et al. |
| 8,211,634 | B2 | 7/2012 | DePinho et al. |
| 8,709,418 | B2 | 4/2014 | Okano et al. |
| 8,828,398 | B2 | 9/2014 | Kobayashi et al. |
| 8,911,740 | B2 | 12/2014 | Saito et al. |
| 2002/0006404 | A1 | 1/2002 | Hanna et al. |
| 2003/0118599 | A1 | 6/2003 | Algate et al. |
| 2003/0190640 | A1 | 10/2003 | Faris et al. |
| 2004/0029114 | A1 | 2/2004 | Mack et al. |
| 2004/0236091 | A1 | 11/2004 | Chicz et al. |
| 2004/0258678 | A1 | 12/2004 | Bodary et al. |
| 2005/0003390 | A1 | 1/2005 | Axenovich et al. |
| 2005/0032113 | A1 | 2/2005 | Tanaka et al. |
| 2005/0244413 | A1 | 11/2005 | Adolf et al. |
| 2006/0019256 | A1 | 1/2006 | Clarke et al. |
| 2006/0069054 | A1 | 3/2006 | Houghton et al. |
| 2006/0275305 | A1 | 12/2006 | Bryant |
| 2007/0048301 | A1 | 3/2007 | Bodary-Winter et al. |
| 2007/0154931 | A1 | 7/2007 | Radich et al. |
| 2007/0264253 | A1 | 11/2007 | Liu et al. |
| 2008/0075722 | A1 | 3/2008 | DePinho et al. |
| 2008/0107668 | A1 | 5/2008 | Philip et al. |
| 2010/0029573 | A1 | 2/2010 | Weinschenk et al. |
| 2010/0068724 | A1 | 3/2010 | Fung et al. |
| 2011/0123492 | A1 | 5/2011 | Okano et al. |
| 2011/0136121 | A1 | 6/2011 | Okano et al. |
| 2011/0189700 | A1 | 8/2011 | Moses et al. |
| 2011/0256144 | A1 | 10/2011 | Okano et al. |

(Continued)

FOREIGN PATENT DOCUMENTS

| CN | 1678338 A | 10/2005 |
| CN | 1705676 A | 12/2005 |

(Continued)

OTHER PUBLICATIONS

GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.

(Continued)

*Primary Examiner* — Sheela J Huff
*Assistant Examiner* — Jessica H Roark
(74) *Attorney, Agent, or Firm* — Birch Stewart Kolasch & Birch LLP

(57) ABSTRACT

This invention provides an antibody targeting a cancer antigenic protein specifically expressed on the surface of cancer cells and use thereof in a therapeutic and/or preventive agent for cancers. Specifically, this invention provides an antibody or a fragment thereof which has immunological reactivity with a partial CAPRIN-1 polypeptide consisting of the amino acid sequence represented by SEQ ID NO: 5 or an amino acid sequence having 80% or higher sequence identity to the amino acid sequence, and a pharmaceutical composition for treatment and/or prevention of cancers, comprising the antibody or fragment thereof as an active ingredient.

20 Claims, No Drawings

(56) References Cited

U.S. PATENT DOCUMENTS

| | | |
|---|---|---|
| 2012/0171699 A1 | 7/2012 | Goodman et al. |
| 2012/0214975 A1 | 8/2012 | Sandig et al. |
| 2012/0294860 A1 | 11/2012 | Ido et al. |
| 2012/0301471 A1 | 11/2012 | Kobayashi et al. |
| 2012/0301476 A1 | 11/2012 | Okano et al. |
| 2012/0321641 A1 | 12/2012 | Okano et al. |
| 2013/0045210 A1 | 2/2013 | Kobayashi et al. |
| 2013/0071398 A1 | 3/2013 | Saito et al. |
| 2014/0179558 A1 | 6/2014 | Ido et al. |
| 2014/0186359 A1 | 7/2014 | Okano et al. |
| 2014/0308283 A1 | 10/2014 | Minamida et al. |
| 2015/0218285 A1 | 8/2015 | Saito et al. |

FOREIGN PATENT DOCUMENTS

| | | |
|---|---|---|
| CN | 101120252 A | 2/2008 |
| CN | 101189516 A | 5/2008 |
| CN | 101836116 A | 9/2010 |
| CN | 102170907 A | 8/2011 |
| CN | 102171570 A | 8/2011 |
| EP | 1557172 A1 | 7/2005 |
| EP | 2 207 037 A1 | 7/2010 |
| EP | 2 325 648 A1 | 5/2011 |
| EP | 2322221 A1 | 5/2011 |
| EP | 2 532 367 A1 | 12/2012 |
| EP | 2 532 743 A1 | 12/2012 |
| EP | 2 832 365 A1 | 2/2015 |
| EP | 2 832 366 A1 | 2/2015 |
| JP | 2002-540790 A | 12/2002 |
| JP | 2003-528587 A | 9/2003 |
| JP | 2006-316040 A | 11/2006 |
| JP | 2013-502205 A | 1/2013 |
| JP | 2013-505028 A | 2/2013 |
| RU | 2234942 C2 | 8/2004 |
| RU | 2306952 C2 | 9/2007 |
| RU | 2006137060 A | 4/2008 |
| WO | WO 00/04149 A2 | 1/2000 |
| WO | WO 00/60077 A2 | 10/2000 |
| WO | WO 01/32910 A2 | 5/2001 |
| WO | WO 01/72295 A2 | 10/2001 |
| WO | WO 02/078524 A2 | 10/2002 |
| WO | WO 02/083070 A2 | 10/2002 |
| WO | WO 02/092001 A2 | 11/2002 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116051 A2 | 12/2005 |
| WO | WO 2005/116076 A2 | 12/2005 |
| WO | WO 2006/002378 A2 | 1/2006 |
| WO | WO 2007/150077 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2009/113742 A1 | 9/2009 |
| WO | WO 2009/117277 A2 | 9/2009 |
| WO | WO 2010/016525 A1 | 2/2010 |
| WO | WO 2010/016526 A1 | 2/2010 |
| WO | WO 2010/016527 A1 | 2/2010 |
| WO | WO 2011/096517 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/096535 A1 | 8/2011 |
| WO | WO 2012/005550 A2 | 1/2012 |
| WO | WO 2012/013609 A1 | 2/2012 |
| WO | WO 2013/018885 A1 | 2/2013 |
| WO | WO 2013/018886 A1 | 2/2013 |
| WO | WO 2013/018894 A1 | 2/2013 |
| WO | WO 013/147169 A1 | 10/2013 |
| WO | WO 2013/147176 A1 | 10/2013 |

OTHER PUBLICATIONS

GenBank Accession No. NM_001111292, Feb. 11, 2008.
GenBank Accession No. NM_016739, Feb. 10, 2008.
GenBank Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
Patent Examination Report No. 1 issued Oct. 14, 2014, in Australian Patent Application No. 2009278387.
GenBank Accession No. NM_005898, Feb. 11, 2008.
De Pascalis et al., "Grafting of "Abbreviated" Complementary-Determining Regions Containing Specificity-Determining Residues Essential for Ligand Contact to Engineer a Less Immunogenic Humanized Monoclonal Antibody," J. Immunol. (2002), vol. 169, pp. 3076-3084.
Extended European Search Report issued Mar. 2, 2015, in European Patent Application No. 12819759.7.
Riechmann et al., "Reshaping Human Antibodies for Therapy," Nature (Mar. 24, 1988), vol. 332, pp. 323-327.
Russian Office Action issued Jan. 28, 2015 in Russian Patent Application No. 2012137502, with partial English translation.
Vajdos et al., "Comprehensive Functional Maps of the Antigen-binding Site of an Anti-ErbB2 Antibody Obtained with Shotgun Scanning Mutagenesis," J. Mol. Biol. (2002), vol. 320, pp. 415-428.
Extended European Search Report issued Mar. 18, 2015, in European Patent Application No. 12820225.6.
Extended European Search Report issued Mar. 23, 2015, in European Patent Application No. 12820596.0.
Non-Final Office Action issued Apr. 14, 2015, in U.S. Appl. No. 14/236,793.
"Gene Symbol Report," Hugo Gene Nomenclature Committee, CAPRIN1, Approved Name: Cell Cycle Associated Protein 1, HGNC ID: HGNC:6743, Nov. 3, 2012, 2 pages.
Akiyoshi, "Cancer Vaccine Therapy Using Peptides Derived from Tumor-rejection Antigens," Jpn. J. Cancer Chemother., vol. 24, No. 5, Mar. 1997, pp. 511-519, with English Abstract (p. 519).
Balmaña et al., "BRCA in breast cancer: ESMO Clinical Recommendations," Annals of Oncology, vol. 20, Supplement 4, 2009, pp. iv19-iv20.
Bodey et al., "Failure of Cancer Vaccines: The Significant Limitations of this Approach to Immunotherapy," Anticancer Research, vol. 20, 2000, pp. 2665-2676.
Bodey et al., "MAGE-1, a cancer/testis-antigen, expression in childhood astrocytomas as an indicator of tumor progression," In Vivo, vol. 16, No. 6, Nov.-Dec. 2002, pp. 583-588 (only one page abstract provided).
Brand et al., "Prospect for Anti-HER2 Receptor Therapy in Breast Cancer," Anticancer Research, vol. 26, 2006, pp. 463-470. 1.
Brass et al., "Translation initiation factor eIF-4gamma is encoded by an amplified gene and induces an immune response in squamous cell lung carcinoma," Human Molecular Genetics, vol. 6, No. 1, 1997, pp. 33-39.
Chamberlain et al., "Innovations and strategies for the development of anticancer vaccines," Expert Opinion on Pharmacotherapy, vol. 1, No. 4, 2000, pp. 603-614.
Chinese Office Action dated Mar. 29, 2013 for Chinese Application No. 200980139037. Only considered for search report.
Chinese Office Action dated May 9, 2013 for Chinese Application No. 201180016730.5 with an English translation.
Comtesse et al., "Probing the human natural autoantibody repertoire using an immunoscreening approach," Clinical & Experimental Immunology, vol. 121, 2000, pp. 430-436.
Ellis et al., "Identification and Characterization of a Novel Protein (p137) Which Transcytoses Bidirectionally in Caco-2 Cells," The Journal of Biological Chemistry, vol. 270, No. 35, Sep. 1, 1995, pp. 20717-20723.
Evans et al.,"Vaccine therapy for cancer-fact or fiction?", Q. J. M ed, Vol, 92, 1999, pp. 299-307.
Extended European Search Report dated Aug. 13, 2013 for European Application No. 11739882.6.
Extended European Search Report dated Aug. 26, 2011 for European Application No, 09805010.7.
Extended European Search Report dated Jan. 30, 2013 for European Application No. 09805009.9.

(56) References Cited

OTHER PUBLICATIONS

Extended European Search Report dated Nov. 6, 2013, for European Application No. 11739876.8.
GeneCards, "Cell Cycle Associated Protein 1—Biological research products for Caprin 1," updated Mar. 19, 2013, 10 pages.
Grill, et al., "Activation/Division of Lymphocytes Results in Increased Levels of Cytoplasmic Activation/Proliferation-Associated Protein-1: Prototype of a New Family of Proteins", The Journal of Immunology, 2004, vol. 172, pp. 2389-2400, XP002690350.
Gü re et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Güre et al., "SSX: A Multigene Family with Several Members Transcribed in Normal Testis and Human Cancer," Int. J. Cancer, vol. 72, 1997, pp. 965-971.
Harlow et al., "Antibodies A Laboratory Manual", Cold Spring Harbor Laboratory, Chapter 3, 1988, pp. 23-34.
International Search Report and Written Opinion of the International Searching Authority (PCT/ISR/210 and PCT/ISA/237), dated Mar. 1, 2011, for International Application No, PCT/JP2011/052413.
International Search Report dated Mar. 8, 2011 for International Application No. PCT/JP2011/052403.
International Search Report dated Mar. 15, 2011 for International Application No. PCT/JP2011/052384.
International Search Report dated Mar. 8, 2011 for International Application No. PCT/JP2011/052414.
International Search Report dated Oct. 6, 2009 for International Application No, PCT/JP2009/063882.
International Search Report dated Sep. 8, 2009 for International Application No. PCT/JP2009/063883.
Itoh et al., "HUB1 is an autoantigen frequently eliciting humoral immune response in patients with adult T cell leukemia," Int. J. Oncol., vol. 14, No. 4, 1999, pp. 703-708 (Abstract only provided).
Jäger et al., "Identification of a tissue-specific putative transcription factor in breast tissue by serological screening of a breast cancer library," Cancer Research, vol. 61, Mar. 1, 2001, pp. 2055-2061.
Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Jungbluth et al., "Immunohistochemical analysis of NY-ESO-1 antigen expression in normal and malignant human tissues," International Journal of Cancer, vol. 92, 2001, pp. 856-860.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Karauzum et al., "Caprin 1 is Frequently Overexpressed in Human Lymphomas," American Society of Human Genetics, Cancer Genetics, Program No. 1190W, Oct. 12, 2011, (Abstract only).
Kataja et al., "Primary breast cancer: ESMO Clinical Recommendations for diagnosis, treatment and follow-up," Annals of Oncology, vol. 20, Supplement 4, 2009, pp. iv10-iv14.
Katsafanas et al., "Colocalization of Transcription and Translation within Cytoplasmic Poxvirus Factories Coordinates Viral Expression and Subjugates Host Functions", Cell Host & Microbe, vol. 2, Oct. 2007, pp. 221-228.
Katsafanas et al., "Vaccinia Virus Intermediate Stage Transcription Is Complemented by Ras-GTPase-activating Protein SH3 Domain-binding Protein (G3BP) . . . ," Jour. of Biol. Chem., vol. 279, No. 50, Dec. 10, 2004, pp. 52210-52217.
Kolobova et al., "Microtubule-dependent association of AKAP350A and CCAR1 with RNA stress granules," Experimental Cell Research, vol. 315, 2009 (Accepted: Nov. 20, 2008), pp. 542-555.
Lu et al., "Identification of an immunological signature of tumor rejection in the neu transgenic mouse," 2007 AACR Annual Meeting, Proceedings Abstract No. 4131, Apr. 14-18, 2007 (Presentation conducted on Apr. 17, 2007) (Abstract only provided).
Lu et al., "Targeting serum antibody for cancer diagnosis: a focus on colorectal cancer," Oncologic, Endocrine & Metabolic, Expert Opinion on Therapeutic Targets, vol. 11, No. 2, Feb. 2007, pp. 235-244.
Müller-Pillasch et al., "Identification of a new tumour-associated antigen TM4SF5 and its expression in human cancer," Gene, vol. 208, 1998, pp. 25-30. I.
Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.
NCBI Reference Sequence, caprin-1 [Bos taurus], Feb. 23, 2013, Accession No. NP001069530, XP615677, 1 page.
NCBI Reference Sequence, caprin-1 [Gallus gallus], Feb. 22, 2013, Accession No. NP001026536, XP423820, 1 page.
NCBI Reference Sequence, caprin-1 isoform 1 [*Homo sapiens*], Mar. 17, 2013, Accession No. NP005889, 3 pages.
NCBI Reference Sequence, caprin-1 isoform 2 [*Homo sapiens*], Mar. 3, 2013, Accession No. NP976240, 3 pages.
NCBI Reference Sequence, caprin-1 isoform a [Mus musculus], Mar. 23, 2013, Accession No. NP058019, 3 pages.
NCBI Reference Sequence, caprin-1 isoform b [Mus musculus], Mar. 23, 2013, Accession No. NP001104760, 3 pages.
NCBI Reference Sequence, caprin-1 isoform c [Mus musculus], Mar. 23, 2013, Accession No. NP001104761,4 pages.
NBCI Reference Sequence, Predicted: caprin-1 [Equus caballus], Jun. 27, 2011, Accession No. XP001492799, 1 page.
NCBI Reference Sequence, Predicted: caprin-1 isoform 2 [Canis lupus familiaris], Dec. 2, 2011, Accession No. XP858109, 1 page.
Nelson et al., "Screening for Breast Cancer: An Update for the U.S. Preventive Services Task Force", Annals of Internal Medicine, vol. 151, No. 10, Nov. 17, 2009, pp. 727-737.
Okano et al., "Abstract 519: Identification of a novel target for antibody therapy of breast cancer", Cancer Research, XP-002700046, vol. 72, Issue 8, Supplemental 1, Apr. 15, 2012, 2 pages.
Pegram et al., "Rational Combinations of Trastuzumab With Chemotherapeutic Drugs Used in the Treatment of Breast Cancer," Journal of the National Cancer Institute, vol. 96, No. 10, May 19, 2004, pp. 739-749.
Polyak et al., "Alanine-170 and proline-172 are critical determinants for extracellular CD20 epitopes; heterogeneity in the fine specificity of CD20 monoclonal antibodies is defined by additional requirements imposed by both amino acid sequence . . . ", Blood, vol. 99, No. 9, May 1, 2002, pp. 3256-3262.
Punt et al., "Edrecolomab alone or in combination with fluorouracil and folinic acid in the adjuvant treatment of stage III colon cancer: a randomised study," Lancet, vol. 360, 2002 (Published online Aug. 13, 2002), pp. 671-677.
R & D Systems, "IHC Products & Protocol Guide," printed Jan. 9, 2014, pp. 1-112.
Rauch et al., "SEREX, Proteomex, AMIDA, and beyond: Serological screening technologies for target identification," Proteomics Clin. Appl., vol. 2, 2008, pp. 355-371.
Russian Notice of Allowance, dated Jun. 4, 2013, for Russian Application No. 2011108260/10 with English translation.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," Int. J. Cancer, vol. 76, 1998, pp. 652-658.
Solomon et al., "Distinct Structural Features of Caprin-1 Mediate Its Interaction with G3BP-1 and Its Induction of Phosphorylation of Eukaryotic . . . ," Molecular and Cellular Biology, Mar. 2007 (Published ahead of print: Jan. 8, 2007), vol. 27, No. 6, pp. 2324-2342, XP002690351.

(56) References Cited

OTHER PUBLICATIONS

Strome et al., "A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
U.S. Notice of Allowance dated Aug. 11, 2014 for U.S. Appl. No. 13/577,028.
U.S. Notice of Allowance dated Dec. 2, 2013 for U.S. Appl. No. 13/576,955.
U.S. Notice of Allowance dated May 7, 2014 for U.S. Appl. No. 13/576,953.
U.S. Notice of Allowance dated Sep. 12, 2014 for U.S. Appl. No. 13/577,212.
U.S. Office Action dated Apr. 4, 2014 for U.S. Appl. No. 13/577,028.
U.S. Office Action dated Aug. 19, 2013 for U.S. Appl. No. 13/576,955.
U.S. Office Action dated Aug. 26, 2013 for U.S. Appl. No. 13/576,950.
U.S. Office Action dated Dec. 21, 2012 for U.S. Appl. No. 13/057,515.
U.S. Office Action dated Dec. 21, 2012 for U.S. Appl. No. 13/057,709.
U.S. Office Action dated Jan. 16, 2014 for U.S. Appl. No. 13/057,515.
U.S. Office Action dated Jul. 1, 2013 for U.S. Appl. No. 13/057,515.
U.S. Office Action dated Jul. 1, 2013 for U.S. Appl. No. 13/577,212.
U.S. Office Action dated Jul. 16, 2013 for U.S. Appl. No. 13/057,709.
U.S. Office Action dated Jun. 14, 2013 for U.S. Appl. No. 13/576,969.
U.S. Office Action dated Jun. 19, 2014 for U.S. Appl. No. 13/057,515.
U.S. Office Action dated Mar. 13, 2013 for U.S. Appl. No. 13/576,955.
U.S. Office Action dated Mar. 24, 2014 for U.S. Appl. No. 13/576,969.
U.S. Office Action dated Nov. 15, 2013 for U.S. Appl. No. 13/576,950.
U.S. Office Action dated Nov. 15, 2013 for U.S. Appl. No. 13/576,953.
U.S. Office Action dated Nov. 15, 2013 for U.S. Appl. No. 13/577,028.
U.S. Office Action dated Nov. 2, 2012 for U.S. Appl. No. 13/057,709.
U.S. Office Action dated Nov. 9, 2012 for U.S. Appl. No. 13/057,515.
U.S. Office Action dated Oct. 15, 2013 for U.S. Appl. No. 13/576,969.
U.S. Office Action dated Oct. 21, 2013 for U.S. Appl. No. 13/577,212.
U.S. Office Action dated Sep. 19, 2013 for U.S. Appl. No. 13/577,028.
U.S. Office Action dated Sep. 6, 2013, for U.S. Appl. No. 13/576,953.
Van Der Bruggen et al., "A Gene Encoding an Antigen Recognized by Cytolytic T Lymphocytes on a Human Melanoma," Science, vol. 254, No. 5038, Dec. 13, 1991, pp. 1643-1647 (Also published in J. Immunol., vol. 178, 2007, pp. 2617-2621).
Wang et al., "Absence of Caprin-1 Results in Defects in Cellular Proliferation," The Journal of Immunology, vol. 175, 2005, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.
Bodey et al., "MAGE-1, a Cancer/Testis-Antigen, Expression in Childhood Astrocytomas as an Indicator of Tumor Progression," in vivo (2002) vol. 16, pp. 583-588.
Comtesse et al., "Probing the human natural autoantibody repertoire using an immunoscreening approach," Clin. Exp. Immunol. (2000), vol. 121, pp. 430-436.

International Search Report issued Nov. 18, 2014, in PCT International Application No. PCT/JP2014/071094.
Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.
Jungbluth et al., "Immunohistochemical Analysis of NY-ESO-1 Antigen Expression in Normal and Malignant Human Tissues," Int. J. Cancer (2001), vol. 92, pp. 856-860.
Kohler et al., "Tumor antigen analysis in neuroblastoma by serological interrogation of bioinformatic data," Cancer Science (Nov. 2010), vol. 101, No. 11, pp. 2316-2324.
Nakamura et al. "Gene Expression Profile of Metastatic Human Pancreatic Cancer Cells Depends on the Organ Microenvironment," Cancer Research (Jan. 1, 2007), vol. 67, No. 1, pp. 139-148.
Non-Final Office Action issued Nov. 6, 2014, in U.S. Appl. No. 13/576,950.
Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.
Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.
Gong et al.,"Caprin-1 is a novel microRNA-223 target for regulating the proliferation and invasion of human breast cancer cells", Biomedicine & Pharmacotherapy, vol. 67, 2013, pp. 629-636.
Qiu et al., "Targeting a ribonucleoprotein complex containing the caprin-1 protein and the c-Myc mRNA suppresses tumor growth in mice: an identification of a novel oncotarget", Oncotarget, vol. 6, No. 4, Dec. 10, 2014, pp. 2148-2163.
Sabile et al., "Caprin-1, a novel Cyr61-interacting protein, promotes osteosarcoma tumor growth and lung metastasis in mice", Biochimica et Biophysica Acta, vol. 1832, 2013 (available online Mar. 23, 2013), pp. 1173-1182.
U.S. Office Action for U.S. Appl. No. 13/576,950, dated Mar. 30, 2015.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report issued Feb. 2, 2015, in European Patent Application No. 12819473.5.
Extended European Search Report issued Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.
U.S. Office Action for U.S. Appl. No. 14/379,867, dated Jun. 24, 2015.
Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.
Office Action issued Aug. 14, 2015, in U.S. Appl. No. 14/236,818.
Office Action issued Aug. 20, 2015, in U.S. Appl. No. 14/452,746.
Office Action issued Jul. 3, 2015, in Russian Patent Application No. 2012137503.
Office Action issued Sep. 15, 2015, in U.S. Appl. No. 14/389,266.
Padlan, E. A., "X-Ray Crystallography of Antibodies," Adv. Prot. Chem. (1996), vol. 49, pp. 57-133.

(56) References Cited

OTHER PUBLICATIONS

Saffari et al., "Identification of novel p53 target genes by cDNA AFLP in glioblastoma cells", Cancer Letters, 2009, No. 273, pp. 316-322.

Extended European Search Report for European Application No. 13767612.8, dated Sep. 22, 2015.

Extended European Search Report for European Application No. 13769665.4, dated Sep. 22, 2015.

"Homo sapiens cell cycle associated protein 1, mRNA (cDNA clone MGC:1378 Image:3355481), complete cds," GenBank databases, NCBI, Accession No. BC001731, Sep. 11, 2007, online.

Huang, J. et al, "IgG Isotype Conversion of a Novel Human Anti-carcinoembryonic Antigen Antibody to Increase its Biological Activity," Anticancer Research, 2006, vol. 26, No. 2A, pp. 1057-1063.

Research, 2006, vol. 11, No. 3, pp. 15-16.

SEQUENCE LISTING

```
<160> NUMBER OF SEQ ID NOS: 17

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:

<400> SEQUENCE: 1
cagagggctg ctggctggct aagtccctcc cgctcccggc tctcgcctca ctaggagcgg    60
ctctcggtgc agcgggacag ggcgaagcgg cctgcgccca cggagcgcgc gacactgccc   120
ggaagggacc gccaccttg ccccctcagc tgcccactcg tgatttccag cggcctccgc    180 gcgcgcacg atg ccc tcg gcc acc agc cac agc ggg agc ggc agc aag tcg    231
            Met Pro Ser Ala Thr Ser His Ser Gly Ser Gly Ser Lys Ser
              1               5                  10 tcc gga ccg cca ccg ccg tcg ggt tcc tcc ggg agt gag gcg gcc gcg    279
Ser Gly Pro Pro Pro Pro Ser Gly Ser Ser Gly Ser Glu Ala Ala Ala
 15                  20                  25                  30 gga gcc ggg gcc gcc gcg ccg gct tct cag cac ccc gca acc ggc acc    327
Gly Ala Gly Ala Ala Ala Pro Ala Ser Gln His Pro Ala Thr Gly Thr
                 35                  40                  45 ggc gct gtc cag acc gag gcc atg aag cag att ctc ggg gtg atc gac    375
Gly Ala Val Gln Thr Glu Ala Met Lys Gln Ile Leu Gly Val Ile Asp
             50                  55                  60 aag aaa ctt cgg aac ctg gag aag aaa aag ggt aag ctt gat gat tac    423
Lys Lys Leu Arg Asn Leu Glu Lys Lys Lys Gly Lys Leu Asp Asp Tyr
         65                  70                  75 cag gaa cga atg aac aaa ggg gaa agg ctt aat caa gat cag ctg gat    471
Gln Glu Arg Met Asn Lys Gly Glu Arg Leu Asn Gln Asp Gln Leu Asp
     80                  85                  90
```

```
gcc gtt tct aag tac cag gaa gtc aca aat aat ttg gag ttt gca aaa    519
Ala Val Ser Lys Tyr Gln Glu Val Thr Asn Asn Leu Glu Phe Ala Lys
 95             100                 105                 110 gaa tta cag agg agt ttc atg gca cta agt caa gat att cag aaa aca    567
Glu Leu Gln Arg Ser Phe Met Ala Leu Ser Gln Asp Ile Gln Lys Thr
            115                 120                 125 ata aag aag aca gca cgt cgg gag cag ctt atg aga gaa gaa gct gaa    615
Ile Lys Lys Thr Ala Arg Arg Glu Gln Leu Met Arg Glu Glu Ala Glu
                130                 135                 140 cag aaa cgt tta aaa act gta ctt gag cta cag tat gtt ttg gac aaa    663
Gln Lys Arg Leu Lys Thr Val Leu Glu Leu Gln Tyr Val Leu Asp Lys
        145                 150                 155 ttg gga gat gat gaa gtg cgg act gac ctg aaa caa ggt ttg aat gga    711
Leu Gly Asp Asp Glu Val Arg Thr Asp Leu Lys Gln Gly Leu Asn Gly
    160                 165                 170 gtg cca ata ttg tcc gaa gag gag ttg tca ttg ttg gat gaa ttc tat    759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag    807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa    855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag    903
Lys Pro Val Cys Gly Thr Thr Tyr Lys Val Leu Lys Glu Ile Val Glu
                225                 230                 235 cgt gtt ttt cag tca aac tac ttt gac agc acc cac aac cac cag aat    951
Arg Val Phe Gln Ser Asn Tyr Phe Asp Ser Thr His Asn His Gln Asn
        240                 245                 250 ggg ctg tgt gag gaa gaa gag gca gcc tca gca cct gca gtt gaa gac    999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa   1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa   1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt   1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca   1191
Glu Thr Val Glu Val Val Asn Ser Leu Gln Gln Gln Pro Gln Ala Ala
320                 325                 330 tcc cct tca gta cca gag ccc cac tct ttg act cca gtg gct cag gca   1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg   1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat   1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca   1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa   1431
Gln Asn Met Asp Met Pro Gln Leu Val Cys Pro Pro Val His Ser Glu
400                 405                 410
```

-continued

```
tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460 cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490 gct ggg aca agc aaa cct tta cat agc agt gga atc aat gta aat gca     1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt     1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag     1815
Pro Pro Val Asn Glu Pro Glu Thr Leu Lys Gln Gln Asn Gln Tyr Gln
            530                 535                 540 gcc agt tat aac cag agc ttt tct agt cag cct cac caa gta gaa caa     1863
Ala Ser Tyr Asn Gln Ser Phe Ser Ser Gln Pro His Gln Val Glu Gln
        545                 550                 555 aca gag ctt cag caa gaa cag ctt caa aca gtg gtt ggc act tac cat     1911
Thr Glu Leu Gln Gln Glu Gln Leu Gln Thr Val Val Gly Thr Tyr His
    560                 565                 570 ggt tcc cca gac cag tcc cat caa gtg act ggt aac cac cag cag cct     1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat     2007
Pro Gln Gln Asn Thr Gly Phe Pro Arg Ser Asn Gln Pro Tyr Tyr Asn
                595                 600                 605 agt cgt ggt gtg tct cgt gga ggc tcc cgt ggt gct aga ggc ttg atg     2055
Ser Arg Gly Val Ser Arg Gly Gly Ser Arg Gly Ala Arg Gly Leu Met
            610                 615                 620 aat gga tac cgg ggc cct gcc aat gga ttc aga gga gga tat gat ggt     2103
Asn Gly Tyr Arg Gly Pro Ala Asn Gly Phe Arg Gly Gly Tyr Asp Gly
        625                 630                 635 tac cgc cct tca ttc tct aac act cca aac agt ggt tat aca cag tct     2151
Tyr Arg Pro Ser Phe Ser Asn Thr Pro Asn Ser Gly Tyr Thr Gln Ser
    640                 645                 650 cag ttc agt gct ccc cgg gat tac tct ggc tat caa cgg gat gga tat     2199
Gln Phe Ser Ala Pro Arg Asp Tyr Ser Gly Tyr Gln Arg Asp Gly Tyr
655                 660                 665                 670 cag cag aat ttc aag cga ggc tct ggg cag agt gga cca cgg gga gcc     2247
Gln Gln Asn Phe Lys Arg Gly Ser Gly Gln Ser Gly Pro Arg Gly Ala
                675                 680                 685 cca cga ggt cgt gga ggg ccc cca aga ccc aac aga ggg atg ccg caa     2295
Pro Arg Gly Arg Gly Gly Pro Pro Arg Pro Asn Arg Gly Met Pro Gln
            690                 695                 700 atg aac act cag caa gtg aat taa tctgattcac aggattatgt ttaatcgcca    2349
Met Asn Thr Gln Gln Val Asn
            705 aaaacacact ggccagtgta ccataaatatg ttaccagaag agttattatc tatttgttct  2409
```

```
cccttttcagg aaacttattg taaagggact gttttcatcc cataaagaca ggactacaat    2469
tgtcagcttt ctattacctg gatatggaag gaaactattt ttactctgca tgttctgtcc    2529
taagcgtcat cttgagcctt gcacatgata ctcagattcc tcacccttgc ttaggagtaa    2589
aacaatatac tttacagggt gataataatc tccatagtta tttgaagtgg cttgaaaaag    2649
gcaagattga cttttatgac attggataaa atctacaaat cagccctcga gttattcaat    2709
gataactgac aaactaaatt atttccctag aaaggaagat gaaaggagtg gagtgtggtt    2769
tggcagaaca actgcatttc acagcttttc cagttaaatt ggagcactga acgttcagat    2829
gcataccaaa ttatgcatgg gtcctaatca cacatataag gctggctacc agcttttgaca   2889 cagcactgtt catctggcca aacaactgtg gttaaaaaca catgtaaaat gcttttttaac   2949 agctgatact gtataagaca aagccaagat gcaaaattag gctttgattg gcacttttttg   3009 aaaaatatgc aacaaatatg ggatgtaatc cggatggccg cttctgtact taatgtgaaa    3069
tatttagata cctttttgaa cacttaacag tttctttgag acaatgactt ttgtaaggat    3129
tggtactatc tatcattcct tatgcatgt acattgtctg tcactaatcc ttggattttg    3189
ctgtattgtc acctaaattg gtacaggtac tgatgaaaat ctctagtgga taatcataac    3249
actctcggtc acatgttttt ccttcagctt gaaagctttt ttttaaaagg aaaagatacc    3309
aaatgcctgc tgctaccacc cttttcaatt gctatctttt gaaaggcacc agtatgtgtt    3369
ttagattgat ttccctgttt cagggaaatc acggacagta gtttcagttc tgatggtata    3429
agcaaaacaa ataaaacgtt tataaaagtt gtatcttgaa acactggtgt tcaacagcta    3489
gcagcttatg tgattcaccc catgccacgt tagtgtcaca aatttttatgg tttatctcca   3549 gcaacatttc tctagtactt gcacttatta tcttttgtct aatttaaccct taactgaatt   3609 ctccgtttct cctggaggca tttatattca gtgataattc cttcccttag atgcataggg    3669
agagtctcta aatttgatgg aaatggacac ttgagtagtg acttagccttt atgtactctg   3729 ttggaatttg tgctagcagt ttgagcacta gttctgtgtg cctaggaagt taatgctgct    3789
tattgtctca ttctgacttc atggagaatt aatcccacct ttaagcaaag gctactaagt    3849
taatggtatt ttctgtgcag aaattaaatt ttattttcag catttagccc aggaattctt    3909
ccagtaggtg ctcagctatt taaaaacaaa actattctca aacattcatc attagacaac    3969
tggagttttt gctggttttg taacctacca aaatggatag gctgttgaac attccacatt    4029
caaaagtttt gtagggtggt gggaaatggg ggatcttcaa tgtttatttt aaaataaaat    4089
aaaataagtt cttgactttt ctcatgtgtg gttgtggtac atcatattgg aagggttaac    4149
ctgttacttt ggcaaatgag tattttttttg ctagcacctc cccttgcgtg ctttaaatga   4209
catctgcctg ggatgtacca caaccatatg ttacctgtat cttaggggaa tggataaaat    4269
atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaagggatg ggggagaaaa tgccttctag    4449
gttttgaact tctatgcatt agtgcagatg ttgtgaatgt gtaaaggtgt tcatagtttg    4509 actgttcta tgtatgtttt ttcaaagaat tgttcctttt tttgaactat aatttttctt     4569 ttttttggtta ttttaccatc acagtttaaa tgtatatctt ttatgtctct actcagacca   4629 tattttttaaa ggggtgcctc attatggggc agagaacttt tcaataagtc tcattaagat   4689
ctgaatcttg gttctaagca ttctgtataa tatgtgattc cttgtcctag ctgcagaagg    4749
ccttttgttt ggtcaaatgc atattttagc agagtttcaa ggaaatgatt gtcacacatg    4809
```

-continued

```
tcactgtagc ctcttggtgt agcaagctca catacaaaat acttttgtat atgcataata    4869
taaatcatct catgtggata tgaaacttct tttttaaaac ttaaaaggt agaatgttat     4929 tgattacctt gattagggca gttttatttc cagatcctaa taattcctaa aaaatatgga   4989
aaagtttttt ttcaatcatt gtaccttgat attaaaacaa atatccttta agtatttcta   5049
atcagttagc ttctacagtt cttttgtctc cttttatatg cagctcttac gtgggagact   5109
tttccactta aaggagacat agaatgtgtg cttattctca gaaggttcat taactgaggt   5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
tcattttatg tttaagctcc tgaatctgca ttccacttgg gttgttttta agcattctaa    5349
attttagttg attataagtt agatttcaca gaatcagtat tgcccttgat cttgtccttt    5409
ttatggagtt aacggggagg aagacccctc aggaaaacga aagtaaattg ttaaggctca   5469
tcttcatacc ttttttccatt ttgaatccta caaaaatact gcaaaagact agtgaatgtt   5529
taaaattaca ctagattaaa taatatgaaa gtc                                5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
                35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
            115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
            195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240
```

```
Phe Gln Ser Asn Tyr Phe Asp Ser Thr His Asn His Gln Asn Gly Leu
                245                 250                 255
Cys Glu Glu Glu Ala Ala Ser Ala Pro Ala Val Glu Asp Gln Val
            260                 265                 270
Pro Glu Ala Glu Pro Glu Pro Ala Glu Glu Tyr Thr Glu Gln Ser Glu
                275                 280                 285
Val Glu Ser Thr Glu Tyr Val Asn Arg Gln Phe Met Ala Glu Thr Gln
            290                 295                 300
Phe Thr Ser Gly Glu Lys Glu Gln Val Asp Glu Trp Thr Val Glu Thr
305                 310                 315                 320
Val Glu Val Val Asn Ser Leu Gln Gln Gln Pro Gln Ala Ala Ser Pro
                325                 330                 335
Ser Val Pro Glu Pro His Ser Leu Thr Pro Val Ala Gln Ala Asp Pro
                340                 345                 350
Leu Val Arg Arg Gln Arg Val Gln Asp Leu Met Ala Gln Met Gln Gly
                355                 360                 365
Pro Tyr Asn Phe Ile Gln Asp Ser Met Leu Asp Phe Glu Asn Gln Thr
                370                 375                 380
Leu Asp Pro Ala Ile Val Ser Ala Gln Pro Met Asn Pro Thr Gln Asn
385                 390                 395                 400
Met Asp Met Pro Gln Leu Val Cys Pro Pro Val His Ser Glu Ser Arg
                405                 410                 415
Leu Ala Gln Pro Asn Gln Val Pro Val Gln Pro Glu Ala Thr Gln Val
                420                 425                 430
Pro Leu Val Ser Ser Thr Ser Glu Gly Tyr Thr Ala Ser Gln Pro Leu
                435                 440                 445
Tyr Gln Pro Ser His Ala Thr Glu Gln Arg Pro Gln Lys Glu Pro Ile
                450                 455                 460
Asp Gln Ile Gln Ala Thr Ile Ser Leu Asn Thr Asp Gln Thr Thr Ala
465                 470                 475                 480
Ser Ser Ser Leu Pro Ala Ala Ser Gln Pro Gln Val Phe Gln Ala Gly
                485                 490                 495
Thr Ser Lys Pro Leu His Ser Ser Gly Ile Asn Val Asn Ala Ala Pro
                500                 505                 510
Phe Gln Ser Met Gln Thr Val Phe Asn Met Asn Ala Pro Val Pro Pro
                515                 520                 525
Val Asn Glu Pro Glu Thr Leu Lys Gln Gln Asn Gln Tyr Gln Ala Ser
                530                 535                 540
Tyr Asn Gln Ser Phe Ser Ser Gln Pro His Gln Val Glu Gln Thr Glu
545                 550                 555                 560
Leu Gln Gln Glu Gln Leu Gln Thr Val Val Gly Thr Tyr His Gly Ser
                565                 570                 575
Pro Asp Gln Ser His Gln Val Thr Gly Asn His Gln Pro Pro Gln
                580                 585                 590
Gln Asn Thr Gly Phe Pro Arg Ser Asn Gln Pro Tyr Tyr Asn Ser Arg
                595                 600                 605
Gly Val Ser Arg Gly Gly Ser Arg Gly Ala Arg Gly Leu Met Asn Gly
                610                 615                 620
Tyr Arg Gly Pro Ala Asn Gly Phe Arg Gly Gly Tyr Asp Gly Tyr Arg
625                 630                 635                 640
Pro Ser Phe Ser Asn Thr Pro Asn Ser Gly Tyr Thr Gln Ser Gln Phe
                645                 650                 655
```

```
Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
            675                 680                 685

Gly Arg Gly Gly Pro Pro Arg Pro Asn Arg Gly Met Pro Gln Met Asn
        690                 695                 700

Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccccctcagc tgcccactcg tgatttccag cggcctccgc    180 gcgcgcacg atg ccc tcg gcc acc agc cac agc ggg agc ggc agc aag tcg     231
          Met Pro Ser Ala Thr Ser His Ser Gly Ser Gly Ser Lys Ser
            1               5                  10 tcc gga ccg cca ccg ccg tcg ggt tcc tcc ggg agt gag gcg gcc gcg        279
Ser Gly Pro Pro Pro Pro Ser Gly Ser Ser Gly Ser Glu Ala Ala Ala
 15              20                  25                  30 gga gcc ggg gcc gcc gcg ccg gct tct cag cac ccc gca acc ggc acc        327
Gly Ala Gly Ala Ala Ala Pro Ala Ser Gln His Pro Ala Thr Gly Thr
                 35                  40                  45 ggc gct gtc cag acc gag gcc atg aag cag att ctc ggg gtg atc gac        375
Gly Ala Val Gln Thr Glu Ala Met Lys Gln Ile Leu Gly Val Ile Asp
             50                  55                  60 aag aaa ctt cgg aac ctg gag aag aaa aag ggt aag ctt gat gat tac        423
Lys Lys Leu Arg Asn Leu Glu Lys Lys Lys Gly Lys Leu Asp Asp Tyr
 65                  70                  75 cag gaa cga atg aac aaa ggg gaa agg ctt aat caa gat cag ctg gat        471
Gln Glu Arg Met Asn Lys Gly Glu Arg Leu Asn Gln Asp Gln Leu Asp
             80                  85                  90 gcc gtt tct aag tac cag gaa gtc aca aat aat ttg gag ttt gca aaa        519
Ala Val Ser Lys Tyr Gln Glu Val Thr Asn Asn Leu Glu Phe Ala Lys
 95                 100                 105                 110 gaa tta cag agg agt ttc atg gca cta agt caa gat att cag aaa aca        567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa        615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa        663
Gln Lys Arg Leu Lys Thr Val Leu Glu Leu Gln Tyr Val Leu Asp Lys
        145                 150                 155 ttg gga gat gat gaa gtg cgg act gac ctg aaa caa ggt ttg aat gga        711
Leu Gly Asp Asp Glu Val Arg Thr Asp Leu Lys Gln Gly Leu Asn Gly
    160                 165                 170 gtg cca ata ttg tcc gaa gag gag ttg tca ttg gat gaa ttc tat            759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag        807
```

```
                Lys Leu Val Asp Pro Glu Arg Asp Met Ser Leu Arg Leu Asn Glu Gln
                                195                 200                 205 tat gaa cat gcc tcc att cac ctg tgg gac ctg ctg gaa ggg aag gaa         855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag         903
Lys Pro Val Cys Gly Thr Thr Tyr Lys Val Leu Lys Glu Ile Val Glu
            225                 230                 235 cgt gtt ttt cag tca aac tac ttt gac agc acc cac aac cac cag aat         951
Arg Val Phe Gln Ser Asn Tyr Phe Asp Ser Thr His Asn His Gln Asn
        240                 245                 250 ggg ctg tgt gag gaa gaa gag gca gcc tca gca cct gca gtt gaa gac         999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa        1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa        1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt        1143
Thr Gln Phe Thr Ser Gly Glu Lys Glu Gln Val Asp Glu Trp Thr Val
            305                 310                 315 gaa acg gtt gag gtg gta aat tca ctc cag cag caa cct cag gct gca        1191
Glu Thr Val Glu Val Val Asn Ser Leu Gln Gln Gln Pro Gln Ala Ala
320                 325                 330 tcc cct tca gta cca gag ccc cac tct ttg act cca gtg gct cag gca        1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg        1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat        1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca        1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa        1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca        1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa        1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa        1575
Pro Leu Tyr Gln Pro Ser His Ala Thr Glu Gln Arg Pro Gln Lys Glu
            450                 455                 460 cca att gat cag att cag gca aca atc tct tta aat aca gac cag act        1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag        1671
Thr Ala Ser Ser Ser Leu Pro Ala Ala Ser Gln Pro Gln Val Phe Gln
480                 485                 490 gct ggg aca agc aaa cct tta cat agc agt gga atc aat gta aat gca        1719
Ala Gly Thr Ser Lys Pro Leu His Ser Ser Gly Ile Asn Val Asn Ala
495                 500                 505                 510
```

-continued

| | | |
|---|---|---|
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                      515                        520                      525 | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>                      530                        535                      540 | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>                      545                        550                      555 | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>        560                      565                      570 | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                      580                        585                      590 | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                          595                        600                      605 | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>                      610                        615                      620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>        625                      630                      635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>                      640                        645                      650 | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                      660                        665                      670 | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>                      675                        680                      685 | 2247 |
| cca cga ggt aat att ttg tgg tgg tga tcctagctcc taagtggagc<br>Pro Arg Gly Asn Ile Leu Trp Trp<br>        690 | 2294 |
| ttctgttctg gccttggaag agctgttaat agtctgcatg ttaggaatac atttatcctt | 2354 |
| tccagacttg ttgctaggga ttaaatgaaa tgctctgttt ctaaaactta atcttggacc | 2414 |
| caaattttaa tttttgaatg atttaatttt ccctgttact atataaactg tcttgaaaac | 2474 |
| tagaacatat tctcttctca gaaaaagtgt ttttccaact gaaaattatt tttcaggtcc | 2534 |
| taaaacctgc taaatgtttt taggaagtac ttactgaaac attttgtaa gacattttttg | 2594 |
| gaatgagatt gaacatttat ataaatttat tattcctctt tcattttttt gaaacatgcc | 2654 |
| tattatattt tagggccaga cacccttta tggccggata agccatagtt aacatttaga | 2714 |
| gaaccatttta gaagtgatag aactaatgga atttgcaatg cctttttggac tctctattagt | 2774 |
| gatataaata tcaagttatt tctgactttt aaacaaaact cccaaattcc taacttattg | 2834 |
| agctatactt aaaaaaaatt acaggtttag agagttttt gttttctttt tactgttgga | 2894 |
| aaactacttc ccattttggc aggaagttaa cctatttaac aattagagct agcatttcat | 2954 |
| gtagtctgaa attctaaatg gttctctgat ttgagggagg ttaaacatca aacaggtttc | 3014 |
| ctctattggc cataacatgt ataaaatgtg tgttaaggag gaattacaac gtactttgat | 3074 |
| ttgaatacta gtagaaactg gccaggaaaa aggtacattt ttctaaaaat taatggatca | 3134 |
| cttgggaatt actgacttga ctagaagtat caaaggatgt ttgcatgtga atgtgggtta | 3194 |
| tgttctttcc caccttgtag catattcgat gaaagttgag ttaactgata gctaaaaatc | 3254 |

-continued

```
tgttttaaca gcatgtaaaa agttattta tctgttaaaa gtcattatac agttttgaat    3314
gttatgtagt ttcttttaa cagtttaggt aataaggtct gttttcattc tggtgctttt    3374
attaattttg atagtatgat gttacttact actgaaatgt aagctagagt gtacactaga    3434
atgtaagctc catgagagca ggtaccttgt ctgtcttctc tgctgtatct attcccaacg    3494
cttgatgatg gtgcctggca catagtaggc actcaataaa tatttgttga atgaatgaa    3553
```

<210> SEQ ID NO 4
<211> LENGTH: 694
<212> TYPE: PRT
<213> ORGANISM: Homo sapiens

<400> SEQUENCE: 4

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320
```

```
Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690

<210> SEQ ID NO 5
<211> LENGTH: 16
<212> TYPE: PRT
<213> ORGANISM: Homo sapiens

<400> SEQUENCE: 5
```

Ala Glu Gln Lys Arg Leu Lys Thr Val Leu Glu Leu Gln Tyr Val Leu
1               5                   10                  15

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 106
<212> TYPE: PRT

<213> ORGANISM: Homo sapiens

<400> SEQUENCE: 7

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 8
<211> LENGTH: 5
<212> TYPE: PRT
<213> ORGANISM: Mus musculus

<400> SEQUENCE: 8

Ser Tyr Val Met His
1               5

<210> SEQ ID NO 9
<211> LENGTH: 17
<212> TYPE: PRT
<213> ORGANISM: Mus musculus

<400> SEQUENCE: 9

Tyr Ile Asn Pro Tyr Asn Asp Gly Thr Lys Tyr Asn Glu Lys Phe Lys
1               5                   10                  15
Gly

<210> SEQ ID NO 10
<211> LENGTH: 11
<212> TYPE: PRT
<213> ORGANISM: Mus musculus

<400> SEQUENCE: 10

Arg Tyr Tyr Tyr Gly Ser Ser Gly Gly Tyr Phe
1               5                   10

<210> SEQ ID NO 11
<211> LENGTH: 112
<212> TYPE: PRT
<213> ORGANISM: Mus musculus

<400> SEQUENCE: 11

Gly Pro Glu Leu Val Lys Pro Gly Ala Ser Val Lys Met Ser Cys Lys
1               5                   10                  15
Ala Ser Gly Tyr Thr Phe Thr Ser Tyr Val Met His Trp Val Lys Gln
            20                  25                  30
Lys Pro Gly Gln Gly Leu Glu Trp Ile Gly Tyr Ile Asn Pro Tyr Asn
        35                  40                  45
Asp Gly Thr Lys Tyr Asn Glu Lys Phe Lys Gly Lys Ala Thr Leu Thr
50                  55                  60

```
Ser Asp Lys Ser Ser Thr Ala Tyr Met Glu Leu Ser Ser Leu Thr
 65                  70                  75                  80

Ser Glu Asp Ser Ala Val Tyr Tyr Cys Ala Arg Arg Tyr Tyr Gly
                 85                  90                  95

Ser Ser Gly Gly Tyr Phe Asp Val Trp Ala Gln Asp His Val Arg Thr
            100                 105                 110

<210> SEQ ID NO 12
<211> LENGTH: 15
<212> TYPE: PRT
<213> ORGANISM: Mus musculus

<400> SEQUENCE: 12

Arg Ala Ser Lys Ser Ile Ser Lys Tyr Leu Ala Trp Tyr Gln Glu
  1               5                  10                  15

<210> SEQ ID NO 13
<211> LENGTH: 7
<212> TYPE: PRT
<213> ORGANISM: Mus musculus

<400> SEQUENCE: 13

Ser Gly Ser Thr Leu Gln Ser
  1               5

<210> SEQ ID NO 14
<211> LENGTH: 9
<212> TYPE: PRT
<213> ORGANISM: Mus musculus

<400> SEQUENCE: 14

Gln Gln His Asn Glu Tyr Pro Tyr Thr
  1               5

<210> SEQ ID NO 15
<211> LENGTH: 108
<212> TYPE: PRT
<213> ORGANISM: Mus musculus

<400> SEQUENCE: 15

Asp Val Gln Ile Thr Gln Ser Pro Ser Tyr Leu Ala Ala Ser Pro Gly
  1               5                  10                  15

Glu Thr Ile Thr Ile Asn Cys Arg Ala Ser Lys Ser Ile Ser Lys Tyr
                 20                  25                  30

Leu Ala Trp Tyr Gln Glu Lys Pro Gly Lys Thr Asn Lys Leu Leu Ile
             35                  40                  45

Tyr Ser Gly Ser Thr Leu Gln Ser Gly Ile Pro Ser Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Tyr
                 85                  90                  95

Thr Phe Gly Gly Gly Thr Lys Leu Glu Ile Lys Arg
            100                 105

<210> SEQ ID NO 16
<211> LENGTH: 336
<212> TYPE: DNA
<213> ORGANISM: Mus musculus

<400> SEQUENCE: 16
```

```
ggacctgagc tggtaaagcc tggggcttca gtgaagatgt cctgcaaggc ttctggatac    60
acattcacta gctatgttat gcactgggtg aagcagaagc ctgggcaggg ccttgagtgg   120
attggatata ttaatcctta caatgatggt actaagtaca atgagaagtt caaaggcaag   180
gccacactga cttcagacaa atcctccagc acagcctaca tggagctcag cagcctgacc   240
tctgaggact ctgcggtcta ttactgtgca aggaggtatt actacggtag tagcgggggg   300
tacttcgatg tctgggcgca ggaccacgta cgcacg                             336

<210> SEQ ID NO 17
<211> LENGTH: 324
<212> TYPE: DNA
<213> ORGANISM: Mus musculus

<400> SEQUENCE: 17
gatgtccaga taacccagtc tccatcttat cttgctgcat ctcctggaga aaccattact    60
attaattgca gggcaagtaa gagcattagc aaatatttag cctggtatca agagaaacct   120
gggaaaacta ataagcttct tatctactct ggatccactt tgcaatctgg aattccatca   180
aggttcagtg gcagtggatc tggtacagat ttcactctca ccatcagtag cctggagcct   240
gaagattttg caatgtatta ctgtcaacag cataatgaat acccgtacac gttcggaggg   300
gggaccaagc tggaaataaa acgg                                          324
```

PHARMACEUTICAL COMPOSITION FOR TREATMENT AND/OR PREVENTION OF CANCER

TECHNICAL FIELD

The present invention relates to novel use of an antibody against CAPRIN-1 or a fragment thereof in a drug such as a therapeutic and/or preventive agent for cancer.

BACKGROUND ART

Cancer is the leading cause of death. This disease is currently treated principally by surgical therapy in combination with radiation therapy and/or chemotherapy. In spite of recent development of novel surgical techniques or discovery of novel anticancer agents, the existing treatment of cancer has an insufficiently improved outcome, except for some cancer types. With recent advances of molecular biology or cancer immunology, antibodies that specifically react with cancer, cancer antigens that are recognized by cytotoxic T cells, genes encoding such cancer antigens, and the like have been identified, raising expectations on specific cancer therapy targeting the cancer antigens (Non Patent Literature 1).

For reducing the adverse reaction of cancer therapy, it is desired that peptides, polypeptides, or proteins recognized as antigens of the cancer should rarely exist in normal cells and specifically exist in cancer cells. In 1991, Boon et al. (Ludwig Institute for Cancer Research, Belgium) isolated a human melanoma antigen MAGE1 recognized by CD8-positive T cells by a cDNA expression cloning method using autologous cancer cell lines and cancer-reactive T cells (Non Patent Literature 2). Then, a SEREX (serological identification of antigens by recombinant expression cloning) method has been reported, which adopts a gene expression cloning approach to identify tumor antigens recognized by antibodies produced in response to autologous cancer in vivo in a cancer patient (Non Patent Literature 3 and Patent Literature 1). According to this method, some cancer antigens that are rarely expressed in normal cells and are specifically expressed in cancer have been isolated (Non Patent Literatures 4 to 9). In addition, cell therapy using immunocytes that specifically react with cancer antigens or cancer-specific immunotherapy using vaccines or the like comprising cancer antigens is under clinical trial targeting some of the isolated cancer antigens.

In recent years, various antibody drugs for cancer treatment targeting antigenic proteins on cancer cells have emerged in the world. These drugs have received attention because of their certain efficacy as cancer-specific therapeutic agents. A large majority of antigenic proteins targeted by the drugs, however, are also expressed in normal cells. As a result of administering the antibodies, cancer cells as well as normal cells expressing the antigens are damaged, disadvantageously resulting in adverse reaction. Thus, if cancer antigens specifically expressed on the surface of cancer cells can be identified and antibodies targeting the antigens can be used as drugs, these antibody drugs can be expected to achieve treatment with less adverse reaction.

Cytoplasmic- and proliferation-associated protein 1 (CAPRIN-1) has been known as an intracellular protein that is expressed upon activation or cell division of resting normal cells and forms cytoplasmic stress granules with intracellular RNAs to participate in the regulation of transport and translation of mRNAs. This protein has been found to be specifically expressed on the surface of cancer cells and is under study as a target of antibody drugs for cancer treatment (Patent Literature 2).

PRIOR ART LITERATURE

Patent Literature

Patent Literature 1: U.S. Pat. No. 5,698,396
Patent Literature 2: WO2010/016526

Non Patent Literature

Non Patent Literature 1: Tsuyoshi Akiyoshi, "Japanese Journal of Cancer and Chemotherapy", 1997, Vol. 24, p. 55-519 (Japanese Journal of Cancer and Chemotherapy Publishers Inc., Japan)
Non Patent Literature 2: Bruggen P. et al., Science, 254: 1643-1647 (1991)
Non Patent Literature 3: Proc. Natl. Acad. Sci. USA, 92: 11810-11813 (1995)
Non Patent Literature 4: Int. J. Cancer, 72: 965-971 (1997)
Non Patent Literature 5: Cancer Res., 58: 1034-1041 (1998)
Non Patent Literature 6: Int. J. Cancer, 29: 652-658 (1998)
Non Patent Literature 7: Int. J. Oncol., 14: 703-708 (1999)
Non Patent Literature 8: Cancer Res., 56: 4766-4772 (1996)
Non Patent Literature 9: Hum. Mol. Genet 6: 33-39, 1997

SUMMARY OF INVENTION

Problem to be Solved by Invention

An object of the present invention is to produce an antibody that targets CAPRIN-1 specifically expressed on the surface of cancer cells and is superior in antitumor activity to conventional antibodies, and to provide use thereof as a therapeutic and/or preventive agent for cancer.

Means for Solving Problem

Features of the present invention are as follows:
The present invention provides an antibody or a fragment thereof which has immunological reactivity with a partial CAPRIN-1 polypeptide having the amino acid sequence represented by SEQ ID NO: 5 or an amino acid sequence having 80% or higher sequence identity to the amino acid sequence, and a pharmaceutical composition for treatment and/or prevention of cancer, comprising the antibody or fragment thereof as an active ingredient.

In the above embodiment, the cancer is breast cancer, kidney cancer, pancreatic cancer, colorectal cancer, lung cancer, brain tumor, gastric cancer, uterine cervix cancer, ovary cancer, prostate cancer, bladder cancer, esophageal cancer, leukemia, lymphoma, fibrosarcoma, mastocytoma, or melanoma.

In one embodiment, the antibody is a monoclonal antibody or a polyclonal antibody.

In another embodiment, the antibody is a human antibody, a humanized antibody, a chimeric antibody, a single-chain antibody, or a multispecific antibody (e.g., a bispecific antibody).

The present specification encompasses the contents described in the specification and/or drawings of Japanese Patent Application No. 2012-035484 from which the present application claims the priority.

Effect of Invention

The antibody against CAPRIN-1 according to the present invention damages cancer cells. Thus, the antibody against CAPRIN-1 is useful in the treatment or prevention of cancers.

MODE FOR CARRYING OUT INVENTION

The antibody according to the present invention is an antibody that recognizes and binds to a predetermined partial polypeptide of CAPRIN-1 and has antitumor activity. More specifically, the antibody according to the present invention is an antibody that recognizes (i.e., has immunological reactivity with) a partial polypeptide of a CAPRIN-1 protein (partial CAPRIN-1 polypeptide) consisting of the amino acid sequence represented by SEQ ID NO: 5 or an amino acid sequence having 80% or higher, preferably 85% or higher, more preferably 90% or higher, further preferably 95% or higher sequence identity to the amino acid sequence of SEQ ID NO: 5. In the present invention, it is revealed that this antibody exhibits antitumor activity. The present invention relates to all antibodies that bind to fragments of CAPRIN-1 proteins as described above and exhibit antitumor activity.

The antibody against CAPRIN-1 according to the present invention may be any type of antibody, with the proviso that it can exert antitumor activity, and includes, for example, recombinant antibodies (e.g., synthetic antibodies, multispecific antibodies (e.g., bispecific antibodies), humanized antibodies, chimeric antibodies, and single-chain antibodies (scFv)), human antibodies, and antibody fragments thereof (e.g., Fab, F(ab')$_2$, and Fv). These antibodies and fragments thereof can be prepared by methods generally known to those skilled in the art. Desirably, the antibody according to the present invention has immunological reactivity with a CAPRIN-1 protein or a partial polypeptide thereof, or binds to (preferably, specifically binds to) the CAPRIN-1 protein through antigen-antibody reaction. As used herein, the term "specifically binding to the CAPRIN-1 protein" means that the antibody specifically binds to the CAPRIN-1 protein without substantially binding to other proteins. The antibody according to the present invention is preferably a monoclonal antibody and however, may be a polyclonal antibody as long as homogeneous antibodies can be stably produced. In the case that the subject is a human, human antibodies or humanized antibodies are desirable for avoiding or suppressing rejection.

The antibody against a CAPRIN-1 polypeptide according to the present invention can be evaluated for its antitumor activity, as described later, by examining in vivo the inhibition of tumor growth in a cancer-bearing animal or by examining in vitro whether or not the antibody exhibits immunocyte- or complement-mediated cytotoxic activity against tumor cells expressing the polypeptide.

The subject in need of the treatment and/or prevention of cancer according to the present invention is a mammal such as a human, a pet animal, livestock, or a sport animal, preferably a human.

Hereinafter, the present invention will be described in more detail.

<Preparation of Antigen for Antibody Preparation>

Proteins or fragments thereof used as sensitizing antigens for obtaining the antibody against CAPRIN-1 according to the present invention are not limited by animal species serving as their origins, including humans, dogs, cats, cattle, horses, mice, rats, and chickens. The proteins or the fragments thereof, however, are preferably selected in view of compatibility with parent cells for use in cell fusion. In general, mammal-derived proteins are preferred. Particularly, human-derived proteins are preferred. For example, when CAPRIN-1 is human CAPRIN-1, human CAPRIN-1 protein, partial peptides thereof, or cells expressing human CAPRIN-1 can be used.

The nucleotide sequences and amino acid sequences of human CAPRIN-1 and homologs thereof can be obtained, for example, by making an access to GenBank (NCBI, USA) and using an algorithm such as BLAST or FASTA (Karlin and Altschul, Proc. Natl. Acad. Sci. USA, 90: 5873-5877, 1993; and Altschul et al., Nucleic Acids Res. 25: 3389-3402, 1997).

In the present invention, with reference to the nucleotide sequence (SEQ ID NO: 1 or 3) or the amino acid sequence (SEQ ID NO: 2 or 4) of human CAPRIN-1, the target CAPRIN-1 is a nucleic acid or a protein consisting of a sequence having 70% to 100%, preferably 80% to 100%, more preferably 90% to 100%, further preferably 95% to 100%, for example, 97% to 100%, 98% to 100%, 99% to 100%, or 99.5% to 100% sequence identity to the nucleotide sequence or amino acid sequence of the ORF or mature portion of the reference (Note: when compared with each other, the amino acid sequences of SEQ ID NO: 2 and SEQ ID NO: 4 differ in amino acid residues at position 690 and following position 690). As used herein, the term "% sequence identity" means a percentage (%) of the number of identical amino acids (or nucleotides) to the total number (including the number of gaps) of amino acids (or nucleotides) when two sequences are aligned such that the maximum degree of similarity or identity is achieved with or without gaps introduced.

A fragment that comprises an epitope (or an antigenic determinant), which is a minimal unit recognized by the antibody, and has a length ranging from the amino acid length of the epitope to less than the full-length of the CAPRIN-1 protein can be used as a CAPRIN-1 protein fragment. The epitope refers to a polypeptide fragment having antigenicity or immunogenicity in mammals, preferably humans. Its minimal unit consists of approximately 7 to 12 amino acids, for example, 8 to 11 amino acids. The CAPRIN-1 protein fragment for use in the preparation of the antibody according to the present invention is preferably a fragment that is recognized by the antibody of the present invention and comprises the amino acid sequence represented by SEQ ID NO: 5 (which corresponds to a sequence from positions 141 to 156 in the amino acid sequence of SEQ ID NO: 2 or 4) or an amino acid sequence having 80% or higher, preferably 85% or higher, more preferably 90% or higher, further preferably 95% or higher sequence identity to the amino acid sequence of SEQ ID NO: 5, or comprises at least an epitope consisting of approximately 7 to 12 consecutive amino acids, for example, 8 to 11 consecutive amino acids in any of these amino acid sequences.

The above human CAPRIN-1 proteins and polypeptide fragments comprising partial peptides thereof can be synthesized according to chemical synthesis methods, for example, Fmoc (fluorenylmethyloxycarbonyl) and tBoc (t-butyloxycarbonyl) methods (Seikagaku Jikken Koza (Biochemical Experimentation Course) 1, the Japanese Biochemical Society ed., Protein Chemistry IV, Chemical Modification and Peptide Synthesis, Tokyo Kagaku Dojin Co., Ltd. (Japan), 1981). Also, these polypeptides can be synthesized by routine methods using various commercially available peptide synthesizers.

Alternatively, polynucleotides encoding the polypeptides may be prepared using genetic engineering techniques known in the art (Sambrook et al., Molecular Cloning, the 2nd edition, Current Protocols in Molecular Biology (1989), Cold Spring Harbor Laboratory Press; Ausubel et al., Short Protocols in Molecular Biology, the 3rd edition, A compendium of Methods from Current Protocols in Molecular Biology (1995), John Wiley & Sons; etc.) and incorporated into expression vectors, which are then introduced into host cells so that the host cells produce the polypeptides. In this way, the human CAPRIN-1 proteins of interest or the polypeptide fragments thereof can be obtained.

The polynucleotides encoding the polypeptides can be readily prepared by genetic engineering techniques known in the art or routine methods using commercially available nucleic acid synthesizers. For example, a DNA comprising the nucleotide sequence of a human CAPRIN-1 gene can be prepared by PCR using a human chromosomal DNA or cDNA library as a template and a pair of primers designed so as to be capable of amplifying the nucleotide sequence. Reaction conditions for this PCR can be appropriately determined Examples of the conditions can include, but are not limited to, 30 cycles each involving reaction steps of 94° C. for 30 seconds (denaturation), 55° C. for 30 seconds to 1 minute (annealing), and 72° C. for 2 minutes (elongation) using thermostable DNA polymerase (e.g., Taq polymerase or Pfu polymerase) and a $Mg^{2+}$-containing PCR buffer, followed by reaction at 72° C. for 7 minutes. The PCR approach, conditions, etc. are described in, for example, Ausubel et al., Short Protocols in Molecular Biology, the 3rd edition, A Compendium of Methods from Current Protocols in Molecular Biology (1995), John Wiley & Sons (particularly, Chapter 15).

Also, appropriate probes or primers can be prepared on the basis of information about the nucleotide sequences of CAPRIN-1 genes and the amino acid sequences of CAPRIN-1 proteins, and can be used in the screening of, for example, a human cDNA library, to isolate the desired DNA. Preferably, such a cDNA library is produced from cells, organs, or tissues expressing CAPRIN-1 proteins. Examples of such cells or tissues include cells or tissues derived from the testis or from cancers or tumors such as leukemia, breast cancer, lymphoma, brain tumor, lung cancer, pancreatic cancer, and colorectal cancer. These techniques, including the preparation of probes or primers, the construction of a cDNA library, the screening of the cDNA library, and the cloning of the gene of interest, are known to those skilled in the art and can be performed according to methods described in, for example, Sambrook et al., Molecular Cloning, the 2nd edition, Current Protocols in Molecular Biology (1989), and Ausubel et al. (ibid.). DNAs encoding the human CAPRIN-1 proteins and the partial peptides thereof can be obtained from the DNA thus obtained.

The host cells to receive the expression vectors may be any cell capable of expressing the above polypeptides. Examples of prokaryotic cells include, but are not limited to, *E. coli*. Examples of eukaryotic cells include, but are not limited to: mammalian cells such as monkey kidney cells COS1 and Chinese hamster ovary cells CHO; a human embryonic kidney cell line HEK293; a mouse embryonic skin cell line NIH3T3; yeast cells such as budding yeast and fission yeast cells; silkworm cells; and *Xenopus* egg cells.

In the case of using prokaryotic cells as the host cells, the expression vectors used have an origin that permits replication in the prokaryotic cells, a promoter, a ribosomal binding site, a multicloning site, a terminator, a drug resistance gene, an auxotrophic complementary gene, etc. Examples of expression vectors for *E. coli* can include pUC series, pBluescript II, pET expression systems, and pGEX expression systems. The DNAs encoding the above polypeptides can be incorporated into such expression vectors, with which prokaryotic host cells are then transformed, followed by culture of the obtained transformants so that the polypeptides encoded by the DNAs are expressed in the prokaryotic host cells. In this respect, the polypeptides may be expressed as fusion proteins with other proteins.

In the case of using eukaryotic cells as the host cells, expression vectors for eukaryotic cells having a promoter, a splicing region, a poly(A) addition site, etc. are used as the expression vectors. Examples of such expression vectors can include pKA1, pCDM8, pSVK3, pMSG, pSVL, pBK-CMV, pBK-RSV, EBV, pRS, pcDNA3, and pYES2 vectors. In the same way as above, the DNAs encoding the above polypeptides can be incorporated into such expression vectors, with which eukaryotic host cells are then transformed, followed by culture of the obtained transformants so that the polypeptides encoded by the DNAs are expressed in the eukaryotic host cells. In the case of using expression vectors such as pIND/V5-His, pFLAG-CMV-2, pEGFP-N1, or pEGFP-C1, the polypeptides may be expressed as various fusion proteins tagged with His tag (e.g., $(His)_6$ to $(His)_{10}$), FLAG tag, myc tag, HA tag, GFP, or the like.

The expression vectors can be introduced into the host cells using well known methods such as electroporation, a calcium phosphate method, a liposome method, a DEAE dextran method, microinjection, viral infection, lipofection, and binding with cell-penetrating peptides.

The polypeptide of interest can be isolated and purified from the host cells by a combination of separation techniques known in the art. Examples thereof include, but are not limited to, treatment with a denaturant (e.g., urea) or surfactant, ultrasonication, enzymatic digestion, salting-out, solvent fractionation and precipitation, dialysis, centrifugation, ultrafiltration, gel filtration, SDS-PAGE, isoelectric focusing, ion-exchange chromatography, hydrophobic chromatography, affinity chromatography, and reverse-phase chromatography.

The antigens thus prepared can be used as sensitizing antigens as described later for producing the antibody according to the present invention.

<Structure of Antibody>

Antibodies (immunoglobulins) are usually heteromultimeric glycoproteins each comprising at least two heavy chains and two light chains. The immunoglobulins, except for IgM, are heterotetrameric glycoproteins of approximately 150 kDa each composed of two identical light (L) chains and two identical heavy (H) chains. Typically, each light chain is connected to a heavy chain via a single disulfide covalent bond, while the number of disulfide bonds between heavy chains varies among different immunoglobulin isotypes. Each of the heavy and light chains also has an intrachain disulfide bond. Each heavy chain has a variable domain (VH region) at one end, followed by a series of constant regions. Each light chain has a variable domain (VL region) at one end and has a single constant region at the other end. The light chain constant region is aligned with the first heavy chain constant region, while the light chain variable domain is aligned with the heavy chain variable domain. Particular regions called complementarity determining regions (CDRs) in the antibody variable domains exhibit specific variability and impart binding specificity to the antibody. Portions relatively conserved in the variable regions are called framework regions (FRs). The complete heavy and light chain variable domains each comprise four FRs connected via three CDRs. These three CDRs are called CDRH1, CDRH2, and CDRH3 in this order from the N-terminus of the heavy chain. Likewise, the CDRs are called CDRL1, CDRL2, and CDRL3 in the light chain. CDRH3 is the most important in view of the binding specificity of the antibody for its antigen. In addition, CDRs in each chain are kept close to each other via the FR regions and contribute to the formation of an antigen-binding site in the antibody, together with CDRs in the other chain. The constant regions do not directly contribute to antibody-antigen binding, but exhibit various effector functions, for example, involvement in antibody-dependent cellular cytotoxicity (ADCC), phagocytosis mediated by binding to an Fcγ receptor, half-life/clearance rate mediated by a neonatal Fc receptor (FcRn), and complement-dependent cytotoxicity (CDC) mediated by a C1q component in the complement cascade.

<Preparation of Antibody>

The anti-CAPRIN-1 antibody according to the present invention means an antibody having immunological reactivity with a full-length CAPRIN-1 protein or a fragment thereof. Particularly, the anti-CAPRIN-1 antibody of the present invention is an antibody immunologically binding to a partial polypeptide of a CAPRIN-1 protein (partial CAPRIN-1 polypeptide) that is a peptide consisting of the epitope-containing amino acid sequence represented by SEQ ID NO: 5 or a polypeptide consisting of an amino acid sequence having 80% or higher, preferably 85% or higher, more preferably 90% or higher, further preferably 95% or higher sequence identity to the amino acid sequence. Preferably, the antibody of the present invention recognizes an epitope consisting of approximately 7 to 12 consecutive amino acids, for example, 8 to 11 consecutive amino acids, in the amino acid sequence represented by SEQ ID NO: 5 or the amino acid sequence having 80% or higher, preferably 85% or higher, more preferably 90% or higher, further preferably 95% or higher sequence identity to the amino acid sequence of SEQ ID NO: 5. This anti-CAPRIN-1 antibody of the present invention is capable of specifically binding to the full-length CAPRIN-1 protein. The antibody of the present invention can be obtained by selecting an antibody immunologically binding to the polypeptide consisting of the amino acid sequence represented by SEQ ID NO: 5 or the polypeptide consisting of the amino acid sequence having 80% or higher, preferably 85% or higher, more preferably 90% or higher, further preferably 95% or higher sequence identity to the amino acid sequence of SEQ ID NO: 5, according to a routine method from among antibodies obtained with CAPRIN-1 proteins or fragments thereof as antigens.

As used herein, the term "immunological reactivity" means the property of the antibody binding to a CAPRIN-1 antigen (a full-length CAPRIN-1 protein or a partial polypeptide thereof) in vivo. Via such binding to CAPRIN-1, the antibody of the present invention exerts the function of damaging (e.g., killing, suppressing, or regressing) tumor cells. The antibody of the present invention can damage a tumor, for example, breast cancer, kidney cancer, pancreatic cancer, colorectal cancer (e.g., colon cancer), lung cancer, brain tumor, gastric cancer, uterine cervix cancer, ovary cancer, prostate cancer, bladder cancer, esophageal cancer, leukemia, lymphoma, fibrosarcoma, mastocytoma, or melanoma, through binding to the CAPRIN-1 protein.

The antibody of the present invention may be any type of antibody. Examples of the type of the antibody of the present invention include monoclonal antibodies, polyclonal antibodies, synthetic antibodies, multispecific antibodies, human antibodies, humanized antibodies, chimeric antibodies, single-chain antibodies, and antibody fragments (e.g., Fab, F(ab')$_2$, and Fv). Also, the antibody is any class of immunoglobulin molecule, for example, IgG, IgE, IgM, IgA, IgD, or IgY, or any subclass, for example, IgG1, IgG2, IgG3, IgG4, IgA1, or IgA2.

The antibody may be further modified by a modification such as acetylation, formylation, amidation, phosphorylation, PEGylation, or the like, in addition to glycosylation.

Hereinafter, preparation examples of various antibodies will be described.

When the antibody of the present invention is a monoclonal antibody, for example, a breast cancer cell line SK-BR-3 expressing CAPRIN-1 is administered to each mouse for immunization. The spleen is removed from this mouse. After separation of spleen cells, the cells are fused with mouse myeloma cells. Clones producing antibodies having a cancer cell growth inhibitory effect are selected from among the obtained fusion cells (hybridomas). Alternatively, clones producing antibodies binding to a polypeptide consisting of the amino acid sequence represented by SEQ ID NO: 5 or to a polypeptide consisting of an amino acid sequence having 80% or higher sequence identity to the amino acid sequence of SEQ ID NO: 5 may be selected. The hybridomas producing monoclonal antibodies having a cancer cell growth inhibitory effect or the hybridomas producing monoclonal antibodies against the polypeptide of SEQ ID NO: 5 or the like are isolated and cultured. The antibody of the present invention can be prepared by purification from the culture supernatant according to a general affinity purification method.

The monoclonal antibody-producing hybridomas may be prepared, for example, as follows: first, animals are immunized with sensitizing antigens according to a method known in the art. This immunization method generally involves intraperitoneally or subcutaneously injecting the sensitizing antigens to mammals. Specifically, the sensitizing antigens are diluted with or suspended in PBS (phosphate-buffered saline), physiological saline, or the like into an appropriate amount and then mixed, if desired, with an appropriate amount of a conventional adjuvant, for example, a complete Freund's adjuvant. After emulsification, the resulting emulsion is administered to each mammal several times every 4 to 21 days. Alternatively, an appropriate carrier may be used for the immunization with sensitizing antigens.

After confirmation of a rise in the level of the desired antibody in the serum of the mammal thus immunized, immunocytes are collected from the mammal and subjected to cell fusion. Preferred examples of the immunocytes particularly include spleen cells.

Mammalian myeloma cells are used as partner parent cells to be fused with the immunocytes. Various cell lines known in the art, for example, P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), 5194 (Trowbridge, I. S. J. Exp. Med. (1978) 148, 313-323), and R210 (Galfre, G. et al., Nature (1979) 277, 131-133), are preferably used as the myeloma cells.

The cell fusion between the immunocytes and the myeloma cells can be performed basically according to a method known in the art, for example, the method of Kohler and Milstein (Kohler, G. and Milstein, C. Methods Enzymol. (1981) 73, 3-46).

More specifically, the cell fusion is carried out, for example, in the presence of a cell fusion promoter in a conventional nutrient medium. For example, polyethylene glycol (PEG) or Sendai virus (hemagglutinating virus of Japan, HVJ) is used as the fusion promoter. If desired, an auxiliary such as dimethyl sulfoxide may be further added in order to enhance fusion efficiency.

The ratio between the immunocytes and the myeloma cells used can be arbitrarily set. For example, the amount of the immunocytes is preferably set to 1 to 10 times the amount of the myeloma cells. Examples of the medium that can be used in the cell fusion include RPMI1640 and MEM media suitable for the growth of the myeloma cell lines as well as conventional media for use in this type of cell culture. In addition, a serum supplement such as fetal calf serum (FCS) may be used in combination with these media.

For the cell fusion, the immunocytes and the myeloma cells are well mixed in their predetermined amounts in the medium. A PEG solution (average molecular weight: for example, approximately 1,000 to 6,000) preheated to approximately 37° C. is usually added to the mixture at a concentration of 30 to 60% (w/v) and mixed therewith to form the hybridomas of interest. Subsequently, procedures of sequentially adding an appropriate medium and removing the supernatant by centrifugation are preferably repeated to remove cell fusion agents or the like unfavorable for the growth of the hybridomas.

The hybridomas thus obtained are cultured in a conventional selective medium, for example, a HAT medium (which contains hypoxanthine, aminopterin, and thymidine) for selection. This culture in the HAT medium is continued for a period (usually, several days to several weeks) sufficient for the death of cells (non-fused cells) other than the hybridomas of interest. Subsequently, hybridomas producing the antibody of interest are screened for and cloned as single clones by a conventional limiting dilution method.

In addition to obtaining the hybridomas by immunization of non-human animals with antigens, hybridomas producing human antibodies having the desired activity (e.g., cell growth inhibitory activity) may be obtained by sensitizing human lymphocytes, for example, EB virus-infected human lymphocytes, with proteins, protein-expressing cells, or lysates thereof in vitro and fusing the sensitized lymphocytes with human-derived myeloma cells capable of dividing permanently, for example, U266 (Registration No. TIB196).

The monoclonal antibody-producing hybridomas thus prepared can be subcultured in a conventional medium and can also be stored for a long period in liquid nitrogen.

Specifically, the desired antigens or cells expressing the desired antigens are used as sensitizing antigens in immunization according to a conventional immunization method. The obtained immunocytes are fused with parent cells known in the art according to a conventional cell fusion method. Monoclonal antibody-producing cells (hybridomas) can be screened for by a conventional screening method to prepare the antibody of interest.

Another example of the antibody that may be used in the present invention is a polyclonal antibody. The polyclonal antibody can be obtained, for example, as follows:

Serum is obtained from small animals such as mice, human antibody-producing mice, or rabbits immunized with natural CAPRIN-1 proteins or recombinant CAPRIN-1 proteins expressed as fusion proteins with GST or the like in microorganisms such as E. coli, or partial peptides thereof. Alternatively, serum may be obtained from mammals immunized with CAPRIN-1 fragments serving as sensitizing antigens, i.e., a polypeptide comprising the amino acid sequence represented by SEQ ID NO: 5 or an amino acid sequence having 80% or higher, preferably 85% or higher, more preferably 90% or higher, further preferably 95% or higher sequence identity to the amino acid sequence of SEQ ID NO: 5 (preferably, a polypeptide consisting of any of these amino acid sequences), or a polypeptide comprising an epitope (preferably, consisting of the epitope) consisting of approximately 7 to 12 consecutive amino acids, for example, 8 to 11 consecutive amino acids, in the amino acid sequence represented by SEQ ID NO: 5 or the amino acid sequence having 80% or higher, preferably 85% or higher, more preferably 90% or higher, further preferably 95% or higher sequence identity to the amino acid sequence of SEQ ID NO: 5. The serum thus obtained can be purified using, for example, ammonium sulfate precipitation, protein A or protein G columns, DEAE ion-exchange chromatography, or affinity columns coupled with CAPRIN-1 proteins or synthetic peptides to prepare anti-CAPRIN-1 polyclonal antibodies. The polyclonal antibody of the present invention includes antibodies obtained from human antibody-producing animals (e.g., mice) immunized with CAPRIN-1 protein.

In this context, for example, KM mice (Kirin Pharma Co., Ltd./Medarex) and Xeno mice (Amgen Inc.) are known as the human antibody-producing mice (e.g., International Publication Nos. WO02/43478 and WO02/092812). Complete human polyclonal antibodies can be obtained from the blood of such mice immunized with CAPRIN-1 protein or fragments thereof. Alternatively, spleen cells may be isolated from the mice thus immunized and fused with myeloma cells. In this way, human monoclonal antibodies can be obtained.

The antigens can be prepared according to, for example, a method using animal cells (JP Patent Publication (Kohyo) No. 2007-530068 A (2007)) or a method using baculovirus (e.g., International Publication No. WO98/46777). Antigens having low immunogenicity can be bound to immunogenic macromolecules such as albumin for immunization. The antigens may be administered together with adjuvants for immunization.

Alternatively, the antibody of the present invention may be obtained as a genetically recombinant antibody that is produced using a gene recombination technique which involves: cloning a gene of the antibody from hybridomas; incorporating the antibody gene into appropriate vectors; and introducing the vectors into hosts (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, antibody variable region (V region) cDNAs are synthesized from the mRNAs of hybridomas using reverse transcriptase. After obtainment of DNAs encoding the antibody V regions of interest, the DNAs are ligated with DNAs encoding the desired antibody constant regions (C regions). The resulting ligation products are incorporated into expression vectors. Alternatively, the antibody V region-encoding DNAs may be incorporated into expression vectors containing antibody C region DNAs. These DNAs are incorporated into the expression vectors so as to be expressed under the control of expression control regions, for example, an enhancer and a promoter. Next, host cells can be transformed with the resulting expression vectors and allowed to express antibodies.

The anti-CAPRIN-1 antibody of the present invention is preferably a monoclonal antibody. Alternatively, the anti-CAPRIN-1 antibody of the present invention may be a polyclonal antibody, a genetically engineered antibody (chimeric antibody, humanized antibody, etc.), or the like.

The monoclonal antibody includes human monoclonal antibodies, non-human animal monoclonal antibodies (e.g., mouse, rat, rabbit, and chicken monoclonal antibodies), chimeric monoclonal antibodies, and the like. The monoclonal antibody may be prepared by the culture of hybridomas obtained by the fusion between spleen cells from non-human mammals (e.g., mice, human antibody-producing mice, chickens, or rabbits) immunized with CAPRIN-1 proteins or fragments thereof and myeloma cells. The chimeric antibody is an antibody prepared from a combination of sequences derived from different animals and is, for example, an antibody composed of mouse antibody heavy and light chain variable regions and human antibody heavy and light chain constant regions. The chimeric antibody can be prepared using a method known in the art which involves, for example: ligating DNAs encoding mouse antibody V regions with DNAs encoding human antibody C regions; incorporating the resulting ligation products into expression vectors; and introducing the vectors into hosts so that antibodies are produced.

Monoclonal antibodies that have immunological reactivity with the partial CAPRIN-1 polypeptide consisting of the amino acid sequence represented by SEQ ID NO: 5 and have an antitumor effect are prepared by a method described later in Examples.

The humanized antibody, also called reshaped human antibody, is an engineered antibody. The humanized antibody is constructed by grafting complementarity determining regions (CDRs) of an antibody of an immunized animal at the corresponding complementarity determining regions (CDRs) of a human antibody. A general gene recombination approach therefor is also known.

Specifically, DNA sequences designed so as to link, for example, mouse, rabbit, or chicken antibody CDRs, and human antibody framework regions (FRs) are synthesized by PCR from several prepared oligonucleotides having terminal portions overlapping with each other. The obtained DNAs are ligated with DNAs encoding human antibody constant regions. Subsequently, the resulting ligation products are incorporated into expression vectors, which are then introduced into hosts for antibody production to obtain the antibody of interest (see European Patent Application Publication No. EP239400 and International Publication No. WO96/02576). The human antibody FRs connected via complementarity determining regions (CDRs) are selected such that the CDRs form a favorable antigen-binding site. If necessary, amino acids in the framework regions of antibody variable regions may be substituted such that the complementarity determining regions of the resulting reshaped human antibody form an appropriate antigen-binding site (Sato K. et al., Cancer Research 1993, 53: 851-856). In addition, these FRs may be replaced with framework regions derived from human antibodies of different class or subclass (see International Publication No. WO99/51743).

Amino acids in variable regions (e.g., FRs) or constant regions of the chimeric antibody or the humanized antibody thus prepared may be substituted, for example, by other amino acids.

The amino acid substitution is the substitution of, for example, less than 15, less than 10, 8 or less, 7 or less, 6 or less, 5 or less, 4 or less, 3 or less, or 2 or less amino acids, preferably 1 to 5 amino acids, more preferably 1 or 2 amino acids. The substituted antibody should be functionally equivalent to an unsubstituted antibody. The substitution is desirably conservative amino acid substitution, which is the substitution between amino acids similar in properties such as charge, side chains, polarity, and aromaticity. The amino acids can be classified in terms of similar properties into, for example: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched amino acids (leucine, valine, and isoleucine); and aromatic amino acids (phenylalanine, tyrosine, tryptophan, and histidine).

Examples of modified antibodies can include antibodies bound with various molecules such as polyethylene glycol (PEG). In the modified antibody of the present invention, the substance to be bound is not limited. In order to obtain such a modified antibody, the obtained antibody can be chemically modified. A method therefor has already been established in the art.

As used herein, the term "functionally equivalent" means that an antibody of interest has biological or biochemical activity similar to that of the antibody of the present invention, specifically, the antibody of interest has the function of damaging tumor and essentially causes no rejection when applied to humans, for example. Examples of such activity can include cell growth inhibitory activity and binding activity.

A method for preparing a polypeptide functionally equivalent to a certain polypeptide, which involves introducing a mutation into a polypeptide, is well known to those skilled in the art. For example, those skilled in the art can appropriately introduce a mutation into the antibody of the present invention using site-directed mutagenesis (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. USA. 82, 488-492; and Kunkel (1988) Methods Enzymol. 85, 2763-2766) or the like, thereby preparing an antibody functionally equivalent to the antibody of the present invention.

The antibody that recognizes an epitope of a CAPRIN-1 protein or a CAPRIN-1 fragment polypeptide comprising the epitope can be obtained by a method generally known to those skilled in the art. For example, the antibody can be obtained by a method which involves determining the epitope of the CAPRIN-1 protein recognized by the obtained anti-CAPRIN-1 antibody having a cancer cell growth inhibitory effect by a conventional method (e.g., epitope mapping or an epitope identification method described later) and preparing an antibody using a polypeptide having an amino acid sequence contained in the epitope as an immunogen, or a method which involves determining an epitope for an antibody prepared by a conventional method and selecting an antibody that recognizes the same epitope as that for the anti-CAPRIN-1 antibody. As used herein, the term "epitope" refers to a polypeptide fragment having antigenicity or immunogenicity in mammals, preferably humans. Its minimal unit consists of approximately 7 to 12 amino acids, preferably 8 to 11 amino acids.

The antibody of the present invention is an antibody having immunological reactivity with CAPRIN-1, an antibody that specifically recognizes CAPRIN-1, or an antibody that specifically binds to CAPRIN-1 and exhibits cytotoxic activity against cancer or a tumor growth inhibitory effect. The antibody is preferably an antibody having a structure that causes little or no rejection in recipient animals. Examples of such antibodies include human antibodies, humanized antibodies, chimeric antibodies (e.g., human-mouse chimeric antibodies), single-chain antibodies, and bispecific antibodies when the recipient animals are humans. These antibodies have heavy and light chain variable regions derived from a human antibody or have heavy and light chain variable regions with complementarity determining regions (CDR1, CDR2, and CDR3) derived from a non-human animal antibody and framework regions (FR1, FR2, FR3, and FR4) derived from a human antibody. Alternatively, these antibodies are recombinant antibodies having heavy and light chain variable regions derived from a non-human animal antibody and heavy and light chain constant regions derived from a human antibody. The antibody of the present invention is preferably the former two antibodies.

Such recombinant antibodies can be prepared as follows: DNAs encoding monoclonal antibodies (e.g., human, mouse, rat, rabbit, and chicken monoclonal antibodies) against human CAPRIN-1 are cloned from antibody-producing cells such as hybridomas and used as templates in RT-PCR or the like to prepare DNAs encoding the light and heavy chain variable regions of the antibodies. The respective sequences of the light and heavy chain variable regions, the respective sequences of CDR1, CDR2, and CDR3 in each region, or the respective sequences of FR1, FR2, FR3, and FR4 in each region can be determined on the basis of, for example, the Kabat EU numbering system (Kabat et al., Sequences of Proteins of Immunological Interest, 5th Ed. Public Health Service, National Institute of Health, Bethesda, Md. (1991)).

Such a DNA encoding each variable region or a DNA encoding each CDR is prepared using a gene recombination technique (Sambrook et al., Molecular Cloning A Laboratory Manual, Cold Spring Harbor Laboratory Press (1989)) or a DNA synthesizer. In this context, the human monoclonal antibody-producing hybridomas can be prepared by immunizing human antibody-producing animals (e.g., mice) with human CAPRIN-1 and then fusing spleen cells excised from the immunized animals with myeloma cells. Aside from this, DNAs encoding human antibody-derived light or heavy chain variable and constant regions are prepared, if necessary, using a gene recombination technique or a DNA synthesizer.

For the humanized antibody, DNAs in which the CDR coding sequences in DNAs encoding human antibody-derived light or heavy chain variable regions are substituted by corresponding CDR coding sequences of a non-human animal (e.g., mouse, rat, rabbit, or chicken)-derived antibody can be prepared and ligated with the DNAs encoding human antibody-derived light or heavy chain constant regions to prepare a DNA encoding the humanized antibody.

For the chimeric antibody, DNAs encoding light or heavy chain variable regions of a non-human animal (e.g., mouse, rat, rabbit, or chicken)-derived antibody can be ligated with DNAs encoding human antibody-derived light or heavy chain constant regions to prepare a DNA encoding the chimeric antibody.

The single-chain antibody refers to an antibody comprising heavy and light chain variable regions linearly linked to each other via a linker. A DNA encoding the single-chain antibody can be prepared by ligating a DNA encoding the heavy chain variable region, a DNA encoding the linker, and a DNA encoding the light chain variable region. In this context, the heavy and light chain variable regions are both derived from a human antibody or derived from a human antibody having CDRs alone substituted by CDRs of a non-human animal (e.g., mouse, rat, rabbit, or chicken)-derived antibody. The linker consists of 12 to 19 amino acids. Examples thereof include $(G_4S)_3$ consisting of 15 amino acids (G. B. Kim et al., Protein Engineering Design and Selection 2007, 20 (9): 425-432).

The bispecific antibody (e.g., diabody) refers to an antibody capable of specifically binding to two different epitopes. A DNA encoding the bispecific antibody can be prepared by ligating, for example, a DNA encoding a heavy chain variable region A, a DNA encoding a light chain variable region B, a DNA encoding a heavy chain variable region B, and a DNA encoding a light chain variable region A in this order (provided that the DNA encoding a light chain variable region B and the DNA encoding a heavy chain variable region B are ligated via a DNA encoding a linker as described above). In this context, the heavy and light chain variable regions are all derived from a human antibody or derived from a human antibody having CDRs alone substituted by CDRs of a non-human animal (e.g., mouse, rat, rabbit, or chicken)-derived antibody.

The recombinant DNAs thus prepared can be incorporated into one or more appropriate vectors, which are then introduced into host cells (e.g., mammalian cells, yeast cells, and insect cells) so that the DNAs are (co)expressed to produce recombinant antibodies (P. J. Delves, ANTIBODY PRODUCTION ESSENTIAL TECHNIQUES, 1997 WILEY, P. Shepherd and C. Dean, Monoclonal Antibodies, 2000 OXFORD UNIVERSITY PRESS; and J. W. Goding, Monoclonal Antibodies: principles and practice, 1993 ACADEMIC PRESS).

Examples of the antibody of the present invention prepared by any of the methods described above include the following antibody (a) obtained in Examples described later:

(a) an antibody comprising a heavy chain variable region comprising complementarity determining regions of SEQ ID NOs: 8, 9, and 10 and a light chain variable region comprising complementarity determining regions of SEQ ID NOs: 12, 13, and 14 (e.g., an antibody constituted by a heavy chain variable region of SEQ ID NO: 11 and a light chain variable region of SEQ ID NO: 15).

In this context, the amino acid sequences represented by SEQ ID NOs: 8, 9, and 10 correspond to CDR1, CDR2, and CDR3 of the heavy chain variable region of a mouse-derived antibody, respectively. The amino acid sequences represented by SEQ ID NOs: 12, 13, and 14 correspond to CDR1, CDR2, and CDR3 of the light chain variable region of a mouse-derived antibody, respectively.

Examples of the humanized antibody, the chimeric antibody, the single-chain antibody, or the bispecific antibody of the present invention include the following antibodies (i) to (iii):

(i) an antibody comprising a heavy chain variable region comprising CDR1, CDR2, and CDR3 consisting of the amino acid sequences of SEQ ID NOs: 8, 9, and 10, respectively, and human antibody-derived framework regions, and a light chain variable region comprising CDR1, CDR2, and CDR3 consisting of the amino acid sequences of SEQ ID NOs: 12, 13, and 14, respectively, and human antibody-derived framework regions;

(ii) an antibody comprising a heavy chain comprising a heavy chain variable region comprising CDR1, CDR2, and CDR3 consisting of the amino acid sequences of SEQ ID NOs: 8, 9, and 10, respectively, and human antibody-derived framework regions, and a human antibody-derived heavy chain constant region, and a light chain comprising a light chain variable region comprising CDR1, CDR2, and CDR3 consisting of the amino acid sequences of SEQ ID NOs: 12, 13, and 14, respectively, and human antibody-derived framework regions, and a human antibody-derived a light chain constant region; and (iii) an antibody comprising a heavy chain comprising a heavy chain variable region comprising the amino acid sequence of SEQ ID NO: 11 and a human antibody-derived heavy chain constant region, and a light chain comprising a light chain variable region comprising the amino acid sequence of SEQ ID NO: 15 and a human antibody-derived light chain constant region.

The sequences of the constant and variable regions of human antibody heavy and light chains are available from, for example, NCBI (USA; GenBank, UniGene, etc.). For example, the following sequences can be referred to: Registration No. J00228 for a human IgG1 heavy chain constant region; Registration No. J00230 for a human IgG2 heavy chain constant region; Registration No. X03604 for a human IgG3 heavy chain constant region; Registration No. K01316 for a human IgG4 heavy chain constant region; Registration Nos. V00557, X64135, X64133, etc. for a human light chain κ constant region; and Registration Nos. X64132, X64134, etc. for a human light chain λ constant region.

Preferably, these antibodies have cytotoxic activity and can thereby exert an antitumor effect.

The above particular sequences of the heavy and light chain variable regions and CDRs in each antibody are provided merely for illustrative purposes. It is obvious that the antibody of the present invention is not limited by the particular sequences. Hybridomas capable of producing anti-human CAPRIN-1 human antibodies or non-human animal antibodies (e.g., mouse antibodies) different from those described above are prepared, and monoclonal antibodies produced by the hybridomas are recovered and assessed as being (or being not) the antibodies of interest with immunological binding activity against human CAPRIN-1 and cytotoxic activity as indicators. The monoclonal antibody-producing hybridomas of interest are thereby identified. Then, DNAs encoding the heavy and light chain variable regions of the antibodies of interest are produced from the hybridomas and sequenced, as described above. The DNAs are used for the preparation of the different antibodies.

The above antibodies may each have the substitution, deletion, or addition of one or several amino acids, particularly in a framework region sequence and/or a constant region sequence, as long as the antibody has such specificity that it can specifically recognize CAPRIN-1. As used herein, the term "several" means preferably 2 to 5, more preferably 2 or 3.

The affinity constant Ka ($K_{on}/k_{off}$) of the antibody of the present invention for a CAPRIN-1 protein or a fragment thereof is preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $10^{13}$ $M^{-1}$.

The antibody of the present invention can be conjugated with an antitumor agent. The conjugation of the antibody with the antitumor agent can be performed via a spacer having a group (e.g., a succinimidyl group, a formyl group, a 2-pyridyldithio group, a maleimidyl group, an alkoxycarbonyl group, or a hydroxy group) reactive with an amino group, a carboxyl group, a hydroxy group, a thiol group, or the like.

Examples of the antitumor agent include the following antitumor agents publicly known in literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylornithine (DMFO), retinoic acid, capecitabine, and pharmaceutically acceptable salts and derivatives thereof Alternatively, the antibody of the present invention can be administered in combination with an antitumor agent to produce a higher therapeutic effect. This approach is applicable to a patient with cancer expressing CAPRIN-1 either before or after surgical operation. This approach can be applied, particularly after surgery, to CAPRIN-1-expressing cancer, which has been treated conventionally with an antitumor agent alone, to produce higher prevention of cancer recurrence or prolongation of survival time.

Examples of the antitumor agent used in the combined administration with the antibody of the present invention also include the following antitumor agents publicly known in literatures, etc.: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, Adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocin, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridin A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, Xeloda, ibandronate, irinotecan, topoisomerase inhibitors, difluoromethylornithine (DMFO), retinoic acid, capecitabine, and pharmaceutically acceptable salts (known in the art) and derivatives (known in the art) thereof. Of these antitumor agents, cyclophosphamide, paclitaxel, docetaxel, or vinorelbine is particularly preferably used.

Alternatively, the antibody of the present invention may be bound to a radioisotope publicly known in literatures, etc., such as, $^{211}$At, $^{131}$I, $^{125}$I, $^{90}$Y, $^{186}$Re, $^{188}$Re, $^{153}$Sm, $^{212}$Bi, $^{32}$P, $^{175}$Lu, $^{176}$Lu, $^{89}$Sr, $^{64}$Cu, or $^{111}$In (Hideo Saji, YAKUGAKU ZASSHI 128 (3) 323-332, 8 (2008), Jpn). A radioisotope effective for the treatment or diagnosis of tumor is desirable. Such a radioisotope is also included in the antitumor agent according to the present invention.

<Identification of Epitope>

As shown in Examples below, the antibody of the present invention binds to an epitope in the amino acid sequence represented by SEQ ID NO: 5. One example of a method for confirming an epitope for the antibody of the present invention includes a method which involves immobilizing an epitope in the polypeptide of SEQ ID NO: 5 onto a plate and evaluating the antibody for its reactivity with this epitope. Specifically, an epitope in the polypeptide of SEQ ID NO: 5 is immobilized through reaction onto a plate attached with electron-withdrawing functional groups via spacer such as oligoethylene glycol. The antibody of the present invention can be reacted with the plate and evaluated for its reactivity with the epitope through reaction with a labeled (e.g., horseradish peroxidase (HRP)-labeled) secondary antibody binding to the antibody of the present invention, i.e., the epitope to which the antibody of the present invention binds can be confirmed. The epitope in the polypeptide of SEQ ID NO: 5 used in the immobilization onto a plate is a sequence itself comprising at least the epitope in the sequence of SEQ ID NO: 5 or a modified portion thereof (e.g., N-terminal or C-terminal residues modified with several arbitrary amino acids or a protein such as KLH or a (poly)peptide modified with a MAP protein). The antibody of the present invention needs only to bind to any of these (poly)peptides.

On the other hand, even the antibody of the present invention may be unreactive with the polypeptide of SEQ ID NO: 5, i.e., the epitope may not be confirmed, in the above method. In this case, the antibody is reacted with an antigen under solution conditions that facilitate to bind the antigen and the antibody. After obtainment of an antigen-antibody complex by an immunoprecipitation method, a partial polypeptide bound with the antibody can be separated and examined for its amino acid sequence to confirm the epitope for the antibody of the present invention. In this context, the antigen is, for example, the polypeptide of SEQ ID NO: 5 itself or a modified portion thereof. Alternatively, even a CAPRIN-1 protein may be used as long as the epitope reactive with the antibody of the present invention can be confirmed by the above method.

<Antitumor Effect>

The antitumor effect of the anti-CAPRIN-1 antibody used in the present invention on CAPRIN-1-expressing cancer cells seems to be brought about by the following mechanism: effector cell-mediated antibody-dependent cellular cytotoxicity (ADCC) and complement-dependent cytotoxicity (CDC) against the CAPRIN-1-expressing cells. However, this mechanism is not intended to limit the scope of the present invention.

The antitumor effect based on the mechanism is known to correlate with the number of target molecules expressed on the surface of cancer cells to which the antibody binds (Niwa R., Clinical Cancer Research 2005 Mar. 15; 11 (6): 2327-2336). The number of target molecules expressed on the surface of cancer cells can be examined using an existing assay kit capable of measuring the number of cell surface molecules. Specifically, the number of target molecules to which the antibody binds can be determined by: reacting primary antibodies such as antibodies against the target molecules with cancer cells; reacting therewith fluorescently labeled antibodies against the primary antibodies together with beads for a calibration curve with the known number of molecules; and measuring the mean fluorescence intensity of the samples to obtain a calibration curve.

Thus, the anti-CAPRIN-1 antibody used in the present invention can be evaluated for its activity, as specifically shown in Examples below, by assaying the ADCC or CDC activity against CAPRIN-1-expressing cancer cells in vitro or by examining the number of CAPRIN-1 molecules expressed on the surface of cancer cells using the anti-CAPRIN-1 antibody according to the present invention as a primary antibody.

The anti-CAPRIN-1 antibody used in the present invention binds to a CAPRIN-1 protein on cancer cells and exhibits an antitumor effect through the activity. Thus, the anti-CAPRIN-1 antibody of the present invention is useful in the treatment or prevention of cancer. Thus, the present invention provides a pharmaceutical composition for treatment and/or prevention of a cancer, comprising the anti-CAPRIN-1 antibody as an active ingredient. The anti-CAPRIN-1 antibody used for the purpose of administration to human bodies (antibody therapy) is preferably a human antibody or a humanized antibody for reducing immunogenicity.

An anti-CAPRIN-1 antibody with higher binding affinity for a CAPRIN-1 protein on cancer cell surface exerts stronger antitumor activity. Thus, the antibody of the present invention has high binding affinity for the CAPRIN-1 protein and can therefore be expected to have a stronger antitumor effect. Accordingly, the antibody of the present invention is applicable to a pharmaceutical composition intended for the treatment and/or prevention of a cancer. Such high binding affinity of the antibody of the present invention is preferably at least $10^7$ M$^{-1}$, at least $10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$ M$^{-1}$, or at least $10^{13}$ M$^{-1}$, in terms of an association constant (affinity constant) Ka ($k_{on}/k_{off}$), as described above.

The anti-CAPRIN-1 antibody binding to a larger number of CAPRIN-1 molecules on cancer cell surface produces stronger antitumor activity. Desirably, the number of CAPRIN-1 molecules in assay using the anti-CAPRIN-1 antibody of the present invention is $10^4$ or more, preferably $10^5$ or more, per cancer cell to which the antibody binds in expectation of the antitumor effect. Tumor (cancer cells) having a large number of CAPRIN-1 molecules on the cell surface is particularly preferred as a cancer to receive the antibody of the present invention.

<Binding to Antigen-Expressing Cell>

The ability of the antibody to bind to CAPRIN-1 can be determined by use of binding assay using, for example, ELISA, Western blot, immunofluorescence, and flow cytometry analysis, as described in Examples.

<Immunohistochemical Staining>

The antibody that recognizes CAPRIN-1 can be tested for its reactivity with CAPRIN-1 by an immunohistochemical method well known to those skilled in the art using a paraformaldehyde- or acetone-fixed frozen section or paraformaldehyde-fixed paraffin-embedded section of a tissue obtained from a patient during surgical operation or from an animal carrying a xenograft tissue inoculated with a cell line expressing CAPRIN-1 either spontaneously or after transfection.

For immunohistochemical staining, the antibody reactive with CAPRIN-1 can be stained by various methods. For example, the antibody can be visualized through reaction with a horseradish peroxidase-conjugated goat anti-mouse antibody, goat anti-rabbit antibody, or goat anti-chicken antibody.

<Pharmaceutical Composition and Method for Treating and/or Preventing Cancer>

A target of the pharmaceutical composition for treatment and/or prevention of a cancer of the present invention is not particularly limited as long as the target is a cancer (cells) expressing a CAPRIN-1 gene.

The terms "tumor" and "cancer" used herein mean malignant neoplasm and are used interchangeably with each other.

The cancer targeted in the present invention is a cancer expressing a gene encoding a CAPRIN-1 protein and is preferably breast cancer, kidney cancer, pancreatic cancer, colorectal cancer, lung cancer, brain tumor, gastric cancer, uterine cervix cancer, ovary cancer, prostate cancer, bladder cancer, esophageal cancer, leukemia, lymphoma, fibrosarcoma, mastocytoma, or melanoma.

Specific examples of these cancers include, but are not limited to, breast adenocarcinoma, complex-type breast adenocarcinoma, malignant mixed tumor of mammary gland, intraductal papillary adenocarcinoma, lung adenocarcinoma, squamous cell cancer, small-cell cancer, large-cell cancer, glioma which is tumor of neuroepithelial tissue, ependymoma, neuronal tumor, embryonal neuroectodermal tumor, neurilemmoma, neurofibroma, meningioma, chronic lymphocytic leukemia, lymphoma, gastrointestinal lymphoma, alimentary lymphoma, small to medium cell-type lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal carcinoma, invasive pancreatic ductal carcinoma, pancreatic adenocarcinoma, acinar cell carcinoma, adenosquamous carcinoma, giant cell tumor, intraductal papillary-mucinous neoplasm, mucinous cystic neoplasm, pancreatoblastoma, serous cystadenocarcinoma, solid-pseudopapillary tumor, gastrinoma, glucagonoma, insulinoma, multiple endocrine neoplasia type-1 (Wermer's syndrome), nonfunctional islet cell tumor, somatostatinoma, and VIPoma.

The recipient subjects (patients) are preferably mammals, for example, mammals including primates, pet animals, livestock, and sport animals and are particularly preferably humans, dogs, and cats.

In the case of using the antibody of the present invention as a pharmaceutical composition, the pharmaceutical composition can be formulated by a method generally known to those skilled in the art. For example, the pharmaceutical composition can be used in the form of a parenteral injection of an aseptic solution or suspension with water or any other pharmaceutically acceptable liquid. For example, the pharmaceutical composition may be formulated with the antibody mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. The amount of the active ingredient in such a preparation is determined such that an appropriate dose within the prescribed range can be achieved.

An aseptic composition for injection can be formulated according to conventional pharmaceutical practice using a vehicle such as injectable distilled water.

Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a non-ionic surfactant, for example, polysorbate 80 (TM) or HCO-60.

Examples of oily solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules.

The pharmaceutical composition of the present invention is administered orally or parenterally, preferably parenterally. Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

Also, the administration method can be appropriately selected depending on the age, weight, sex, symptoms, etc. of a patient. The dose of a pharmaceutical composition containing the antibody or a polynucleotide encoding the antibody can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, sex, symptoms, etc. of a patient, those skilled in the art can appropriately select the dose and the method.

The pharmaceutical composition comprising the antibody of the present invention or the fragment thereof can be administered to a subject to treat and/or prevent a cancer, preferably breast cancer, kidney cancer, pancreatic cancer, colorectal cancer, lung cancer, brain tumor, gastric cancer, uterine cervix cancer, ovary cancer, prostate cancer, bladder cancer, esophageal cancer, leukemia, lymphoma, fibrosarcoma, mastocytoma, or melanoma.

The present invention further encompasses a method for treating and/or preventing cancer, comprising administering the pharmaceutical composition of the present invention in combination with the antitumor agent as exemplified above or a pharmaceutical composition comprising the antitumor agent to a subject. The antibody of the present invention or the fragment thereof may be administered simultaneously with or separately from the antitumor agent to the subject. In the case of separately administering these pharmaceutical compositions, either one may be administered first or later. Their dosing intervals, doses, administration routes, and the number of doses can be appropriately selected by a doctor who is a specialist in cancer therapy. The dosage forms of separate drugs to be administered simultaneously also include, for example, pharmaceutical compositions each formulated by mixing the antibody of the present invention or the fragment thereof or the antitumor agent into a pharmacologically acceptable carrier (or medium). The above descriptions about prescription, formulation, administration routes, doses, cancer, etc. as to the pharmaceutical compositions and dosage forms containing the antibody of the present invention are also applicable to any of the above-described pharmaceutical compositions and dosage forms containing the antitumor agent.

Thus, the present invention also provides a combination drug for treatment and/or prevention of a cancer, comprising the pharmaceutical composition of the present invention and a pharmaceutical composition comprising the antitumor agent as exemplified above, and a method for treating and/or preventing cancer, comprising administering the combination drug. The present invention also provides a pharmaceutical composition for treatment and/or prevention of cancer, comprising the antibody of the present invention or the fragment thereof and the antitumor agent together with a pharmacologically acceptable carrier.

<Polypeptide and DNA>

The present invention further provides a DNA encoding the antibody of the present invention or the fragment (antibody-binding fragment) thereof. Such a DNA may be a DNA encoding the heavy and/or light chains of the antibody or may be a DNA encoding the heavy and/or light chain variable regions of the antibody. Such a DNA may also be a DNA encoding each or a combination of the complementarity determining regions of the antibody. Such a DNA includes, for example, a heavy chain variable region-encoding DNA comprising nucleotide sequences encoding the amino acid sequences of SEQ ID NOs: 8, 9, and 10 and a light chain variable region-encoding DNA comprising nucleotide sequences encoding the amino acid sequences of SEQ ID NOs: 12, 13, and 14, in the case of the antibody (a).

The complementarity determining regions (CDRs) encoded by the DNA having these sequences serve as regions that determine the specificity of the antibody. Sequences encoding the other regions (i.e., constant regions and framework regions) of the antibody may therefore be sequences derived from other antibodies. In this context, "other antibodies" also may include antibodies derived from non-human organisms but are preferably those derived from humans from the viewpoint of reducing adverse reactions. Specifically, in the DNA described above, regions encoding each framework region and each constant region in the heavy and light chains preferably comprise nucleotide sequences encoding corresponding human antibody-derived amino acid sequences.

Further examples of the DNA encoding the antibody of the present invention include a heavy chain variable region-encoding DNA comprising a nucleotide sequence encoding the amino acid sequence of SEQ ID NO: 11, and a light chain variable region-encoding DNA comprising a nucleotide sequence encoding the amino acid sequence of SEQ ID NO: 15, in the case of the antibody (a). In this context, the nucleotide sequence encoding the amino acid sequence of SEQ ID NO: 11 is, for example, the nucleotide sequence of SEQ ID NO: 16. The nucleotide sequence encoding the amino acid sequence of SEQ ID NO: 15 is, for example, the nucleotide sequence of SEQ ID NO: 17. When such a DNA comprises a region encoding each constant region in the heavy and light chains, this region preferably comprises a nucleotide sequence encoding a corresponding human antibody-derived amino acid sequence (an amino acid sequence of each constant region in the heavy and light chains).

These antibody DNAs can be obtained, for example, by the methods described above or the following method: first, total RNAs are prepared from hybridomas producing the antibody of the present invention using a commercially available RNA extraction kit, and cDNAs are synthesized using reverse transcriptase and random primers or the like. Subsequently, the antibody-encoding cDNAs are amplified by PCR using, as oligonucleotide primers, conserved sequences of each variable region in known mouse antibody heavy and light chain genes. Sequences encoding the constant regions can be obtained by the PCR amplification of known sequences. The nucleotide sequence of the DNA can be incorporated into a plasmid or a phage for sequencing, for example, and determined according to a routine method.

The present invention further provides the following polypeptides and DNAs related to the antibody (a):

(i) a polypeptide comprising the amino acid sequence of SEQ ID NO: 11, and a DNA encoding the polypeptide (e.g., a DNA comprising the nucleotide sequence of SEQ ID NO: 16);

(ii) a polypeptide comprising the amino acid sequence of SEQ ID NO: 15, and a DNA encoding the polypeptide (e.g., a DNA comprising the nucleotide sequence of SEQ ID NO: 17);

(iii) a heavy chain CDR polypeptide selected from the group consisting of the amino acid sequences represented by SEQ ID NOs: 8, 9, and 10, and a DNA encoding the polypeptide; and (iv) a light chain CDR polypeptide selected from the group consisting of the amino acid sequences represented by SEQ ID NOs: 12, 13, and 14, and a DNA encoding the polypeptide.

These polypeptides and DNAs can be prepared using gene recombination techniques as described above.

SUMMARY OF THE PRESENT INVENTION

The aspects of the present invention described above are summarized below.

(1) An antibody or a fragment thereof which has immunological reactivity with a partial CAPRIN-1 polypeptide consisting of the amino acid sequence represented by SEQ ID NO: 5 or an amino acid sequence having 80% or higher sequence identity to the amino acid sequence.

(2) The antibody or fragment thereof according to (1), wherein the antibody or fragment thereof has cytotoxic activity against a cancer cell expressing a CAPRIN-1 protein.

(3) The antibody or fragment thereof according to (1) or (2), wherein the antibody is a monoclonal antibody or a polyclonal antibody.

(4) The antibody or fragment thereof according to any of (1) to (3), wherein the antibody is a human antibody, a humanized antibody, a chimeric antibody, a single-chain antibody, or a multispecific antibody.

(5) The antibody or fragment thereof according to any of (1) to (4), wherein the antibody or fragment thereof comprises a heavy chain variable region comprising complementarity determining regions of SEQ ID NOs: 8, 9, and 10 (CDR1, CDR2, and CDR3, respectively) and a light chain variable region comprising complementarity determining regions of SEQ ID NOs: 12, 13, and 14 (CDR1, CDR2, and CDR3, respectively) and has immunological reactivity with the CAPRIN-1 protein.

(6) The antibody or fragment thereof according to any of (1) to (5), wherein the antibody or fragment thereof is conjugated with an antitumor agent.

(7) A pharmaceutical composition for treatment and/or prevention of a cancer, comprising an antibody or fragment thereof according to any of (1) to (6) as an active ingredient.

(8) The pharmaceutical composition according to (7), wherein the cancer is breast cancer, kidney cancer, pancreatic cancer, colorectal cancer, lung cancer, brain tumor, gastric cancer, uterine cervix cancer, ovary cancer, prostate cancer, bladder cancer, esophageal cancer, leukemia, lymphoma, fibrosarcoma, mastocytoma, or melanoma.

(9) A combination drug for treatment and/or prevention of cancer, comprising a pharmaceutical composition according to (7) or (8) and a pharmaceutical composition comprising an antitumor agent.

(10) A DNA encoding an antibody or fragment thereof according to any of (1) to (5).

(11) A method for treating and/or preventing cancer, comprising administering an antibody or fragment thereof according to any of (1) to (6), a pharmaceutical composition according to (7) or (8), or a combination drug according to (9) to a subject.

EXAMPLES

Hereinafter, the present invention will be described more specifically with reference to Examples. However, the scope of the present invention is not intended to be limited by these specific examples.

Example 1

Analysis of CAPRIN-1 Expression in Each Tissue

CAPRIN-1 gene expression in canine and human normal tissues and various cell lines was examined by RT-PCR according to Example 1(4) of WO2010/016526. As a result, its strong expression was seen in the testis among the healthy canine tissues, whereas the expression was seen in canine breast cancer and adenocarcinoma tissues. As a result of also confirming the expression in human tissues, the expression was confirmed only in the testis among normal tissues, as with the canine CAPRIN-1 gene. By contrast, the expression was detected in many types of cancer cell lines, including 8 human breast cancer cell lines (ZR75-1, MCF7, T47D, SK-BR-3, MDA-MB-157, BT-20, MDA-MB-231V, and MRK-nu-1) and 4 pancreatic cancer cell lines (Capan-2, MIAPaCa-2, Panc-1, and BxPc-3), among cancer cells. These results demonstrated that CAPRIN-1 is expressed in the breast cancer cell lines and the pancreatic cancer cell lines, though its expression is not seen in normal tissues other than the testis.

Example 2

Preparation of Mouse Monoclonal Antibody Against CAPRIN-1

(1) Preparation of Mouse Monoclonal Antibody

100 µg of a human CAPRIN-1 protein having the amino acid sequence of SEQ ID NO: 2 as prepared in Example 3 of WO2010/016526 was mixed with an equal amount of MPL+ TDM adjuvant (manufactured by Sigma-Aldrich Corp.). This mixture was used as an antigen solution per mouse. The antigen solution was intraperitoneally administered to each 6-week-old Balb/c mouse (manufactured by Japan SLC, Inc.). Then, 7 boosters were performed every 1 week to complete immunization. Three days after the final shot, the spleen of each mouse was excised and ground between two sterilized glass slides. Procedures of washing with PBS(−) (manufactured by Nissui Pharmaceutical Co., Ltd.) and removing the supernatant by centrifugation at 1500 rpm for 10 minutes were repeated three times to obtain spleen cells. The obtained spleen cells were mixed with mouse myeloma cells SP2/0 (purchased from ATCC) at a ratio of 10:1. 200 µl of an RPMI1640 medium containing 10% FBS was heated to 37° C. and mixed with 800 µl of PEG1500 (manufactured by Boehringer Ingelheim GmbH), and the PEG solution thus prepared was added to the cell mixture, which was then left standing for 5 minutes for cell fusion. After removal of the supernatant by centrifugation at 1700 rpm for 5 minutes, the cells were suspended in 150 ml of an RPMI1640 medium containing 15% FBS supplemented with 2% equivalent of a HAT solution (manufactured by Life Technologies, Inc./Gibco) (HAT selective medium). This suspension was inoculated to fifteen 96-well plates (manufactured by Thermo Fisher Scientific Inc./Nunc) at a concentration of 100 µl/well. The spleen cells and the myeloma cells were fused by culture at 37° C. for 7 days under conditions of 5% $CO_2$ to obtain hybridomas.

The prepared hybridomas were screened for the binding affinity of antibodies produced by the hybridomas against CAPRIN-1 proteins as an indicator. A 1 µg/ml solution of the CAPRIN-1 protein prepared by the approach described in Example 3 of WO2010/016526 was added to a 96-well plate at a concentration of 100 µl/well and left standing at 4° C. for 18 hours. Each well was washed three times with PBS-T. Then, a 0.5% bovine serum albumin (BSA) solution (manufactured by Sigma-Aldrich Corp.) was added thereto at a concentration of 400 µl/well and left standing at room temperature for 3 hours. The solution in each well was discarded, and each well was washed three times with 400 µl of PBS-T. Then, the culture supernatant of each hybridoma obtained above was added thereto at a concentration of 100 µl/well and left standing at room temperature for 2 hours. Each well was washed three times with PBS-T. Then, HRP-labeled anti-mouse IgG (H+L) antibody (manufactured by Invitrogen Corp.) diluted 5000-fold with PBS was added thereto at a concentration of 100 µl/well and left standing at room temperature for 1 hour. Each well was washed three times with PBS-T. Then, a TMB substrate solution (manufactured by Thermo Fisher Scientific Inc.) was added thereto at a concentration of 100 µl/well and left standing for 15 to 30 minutes to cause color reaction. After the color development, the reaction was terminated by the addition of 1 N sulfuric acid at a concentration of 100 µl/well. The absorbance was measured at 450 nm and 595 nm using an absorption spectrometer. As a result, several hybridomas producing antibodies having high absorbance were selected.

The selected hybridomas were added to a 96-well plate at a density of 0.5 cells/well and cultured in the plate. One week later, hybridomas forming single colonies in the wells were observed. The cells in these wells were further cultured, and the cloned hybridomas were screened for the binding affinity of antibodies produced by the hybridomas against CAPRIN-1 proteins as an indicator. A 1 µg/ml solution of the CAPRIN-1 proteins prepared in an approach described in Example 3 of WO2010/016526 was added to a 96-well plate at a concentration of 100 µl/well and left standing at 4° C. for 18 hours.

Each well was washed three times with PBS-T. Then, a 0.5% BSA solution was added thereto at a concentration of 400 μl/well and left standing at room temperature for 3 hours. The solution in each well was discarded, and each well was washed three times with 400 μl of PBS-T. Then, the culture supernatant of each hybridoma obtained above was added thereto at a concentration of 100 μl/well and left standing at room temperature for 2 hours. Each well was washed three times with PBS-T. Then, HRP-labeled anti-mouse IgG (H+L) antibody (manufactured by Invitrogen Corp.) diluted 5000-fold with PBS was added thereto at a concentration of 100 μl/well and left standing at room temperature for 1 hour. Each well was washed three times with PBS-T. Then, a TMB substrate solution (manufactured by Thermo Fisher Scientific Inc.) was added thereto at a concentration of 100 μl/well and left standing for 15 to 30 minutes to cause color reaction. After the color development, the reaction was terminated by the addition of 1 N sulfuric acid at a concentration of 100 μl/well. The absorbance was measured at 450 nm and 595 nm using an absorption spectrometer. As a result, 61 hybridoma lines producing monoclonal antibodies reactive with CAPRIN-1 proteins were obtained.

Next, these monoclonal antibodies were screened for antibodies reactive with the surface of breast cancer cells expressing CAPRIN-1. Specifically, $10^6$ cells of a human breast cancer cell line MDA-MB-231V were centrifuged in a 1.5-ml microcentrifuge tube. 100 μl of the culture supernatant of each hybridoma obtained above was added thereto and left standing for 1 hour on ice. After washing with PBS, FITC-labeled goat anti-mouse IgG antibodies (manufactured by Invitrogen Corp.) diluted 500-fold with PBS containing 0.1% FBS were added thereto and left standing for 1 hour on ice. After washing with PBS, the fluorescence intensity was measured using FACSCalibur (Becton, Dickinson and Company). On the other hand, the same operation as above was performed using the serum of each untreated 6-week-old Balb/c mouse diluted 500-fold with a medium for hybridoma culture, instead of the antibodies, to prepare a control. As a result, one monoclonal antibody (anti-CAPRIN-1 antibody #1) having stronger fluorescence intensity than that of the control, i.e., reactive with the surface of breast cancer cells, was selected.

(2) Identification of CAPRIN-1 Epitope Recognized by Anti-CAPRIN-1 Monoclonal Antibody #1

The cancer cell surface-reactive monoclonal antibodies against CAPRIN-1 (anti-CAPRIN-1 antibody #1) obtained in the paragraph (1) were used to identify a CAPRIN-1 epitope region recognized thereby. 93 candidate peptides each consisting of 12 to 16 amino acids in the amino acid sequence of the human CAPRIN-1 protein were synthesized and each dissolved at a concentration of 1 mg/ml in DMSO.

Each peptide was dissolved at a concentration of 30 μg/ml in a 0.1 M sodium carbonate buffer solution (pH 9.6). The solution was added at a concentration of 100 μl/well to a 96-well plate (manufactured by Thermo Fisher Scientific Inc./Nunc, product No.: 436006) and left standing overnight at 4° C. The solution in each well was discarded, and 10 mM ethanolamine/0.1 M sodium carbonate buffer solution (PH 9.6) was added thereto at a concentration of 200 μl/well and left standing at room temperature for 1 hour. Then, the solution in each well was discarded, and each well was washed twice with PBS containing 0.5% Tween 20 (PBST) to prepare a peptide-immobilized plate.

The cell culture supernatant containing the anti-CAPRIN-1 antibody #1 was added at a concentration of 50 μl/well to each plate thus obtained. After shaking at room temperature for 1 hour, the solution in each well was discarded, and each well was washed three times with PBST. Next, a secondary antibody solution containing HRP-labeled anti-mouse IgG (manufactured by Invitrogen Corp.) antibodies diluted 3000- to 4000-fold with PBST was added thereto at a concentration of 50 μl/well. Then, the solution in each well was discarded, and each well was washed six times with PBST.

A TMB substrate solution (manufactured by Thermo Fisher Scientific Inc.) was added thereto at a concentration of 100 μl/well and left standing for 15 to 30 minutes to cause color reaction. After the color development, the reaction was terminated by the addition of 1 N sulfuric acid at a concentration of 100 μl/well. The absorbance was measured at 450 nm and 595 nm using an absorption spectrometer.

As a result, the polypeptide of SEQ ID NO: 5 was identified as a partial sequence of CAPRIN-1 recognized by the anti-CAPRIN-1 antibody #1 obtained in Example 2(1).

(3) Cloning of Variable Region Genes of Anti-CAPRIN-1 Antibody #1

The monoclonal antibodies obtained in Example 2(1) were analyzed for their variable region-encoding gene sequences and amino acid sequences thereof according to the method described in Example 5 of WO2010/016526. As a result, the monoclonal antibody #1 comprised a heavy chain variable region consisting of the amino acid sequence represented by SEQ ID NO: 11 and a light chain variable region consisting of the amino acid sequence represented by SEQ ID NO: 15. A gene sequence encoding the heavy chain variable region of the obtained monoclonal antibody #1 is shown in SEQ ID NO: 16, the amino acid sequence thereof is shown in SEQ ID NO: 11, a gene sequence encoding the light chain variable region thereof is shown in SEQ ID NO: 17, and the amino acid sequence thereof is shown in SEQ ID NO: 15.

It was also shown that: the monoclonal antibody #1 obtained in Example 2(1) comprises the heavy chain variable region consisting of the amino acid sequence represented by SEQ ID NO: 11 and the light chain variable region consisting of the amino acid sequence represented by SEQ ID NO: 15, wherein CDR1, CDR2, and CDR3 in the heavy chain variable region consist of the amino acid sequences represented by SEQ ID NOs: 8, 9, and 10, respectively, and CDR1, CDR2, and CDR3 in the light chain variable region consist of the amino acid sequences represented by SEQ ID NOs: 12, 13, and 14, respectively.

Example 3

Preparation of Polyclonal Antibody Against Partial CAPRIN-1 Polypeptide Present on Cancer Cell Surface In order to obtain polyclonal antibodies against partial CAPRIN-1 polypeptides present on cancer cell surface, a polypeptide (CAPRIN-1-derived peptide shown in SEQ ID NO: 5) comprising the epitope region for the anti-CAPRIN-1 antibody #1 obtained in Example 2, a polypeptide consisting of a region of amino acid residue numbers 50 to 98 in the human CAPRIN-1 amino acid sequence of SEQ ID NO: 2, and a polypeptide consisting of a region of amino acid residue numbers 233 to 305 of SEQ ID NO: 2 were synthesized. 1 mg each of these peptides was mixed as an antigen with an equal volume of an incomplete Freund's adjuvant (IFA) solution. This mixture was subcutaneously administered to each rabbit four times every two weeks. Then, blood was collected to obtain antiserum containing each polyclonal antibody. This antiserum was further purified using a protein G carrier (manufactured by GE Healthcare Bio-Sciences Ltd.) and replaced with PBS to obtain polyclonal antibodies against partial CAPRIN-1 polypeptides present on cancer cell surface. In addition, the serum of a rabbit that received no antigen was purified using a protein G carrier in the same way as above and used as control antibodies.

Example 4

Analysis of CAPRIN-1 Protein Expression on Cancer Cell Membrane Surface

Next, 8 human breast cancer cell lines (ZR75-1, MCF7, T47D, SK-BR-3, MDA-MB-157, BT-20, MDA-MB-231V, and MRK-nu-1) confirmed to have a large level of CAPRIN-1 gene expression were examined for their expression of CAPRIN-1 proteins on the cell surface. $5 \times 10^5$ cells of each human breast cancer cell line thus confirmed to have gene expression were centrifuged in a 1.5-ml microcentrifuge tube. 2 μg (5 μl) each of the polyclonal antibodies against CAPRIN-1-derived peptides (SEQ ID NO: 5) prepared as described above in Example 3 and 95 μl of PBS containing 0.1% fetal bovine serum were added thereto and mixed, and left standing for 1 hour on ice. After washing with PBS, the resulting solution was mixed by the addition of 1 μl of Alexa 488-labeled goat anti-rabbit IgG antibodies (manufactured by Invitrogen Corp.) and 98 μl of PBS containing 0.1% fetal bovine serum (FBS) and left standing for 30 hours on ice. After washing with PBS, the fluorescence intensity was measured using FACSCalibur (Becton, Dickinson and Company). On the other hand, the same operation as above was performed using the control antibodies prepared as described above in Example 3 instead of the polyclonal antibodies against CAPRIN-1-derived peptides to prepare a control. As a result, the cancer cells supplemented with the anti-CAPRIN-1 antibodies all exhibited fluorescence intensity at least 35% stronger than that of the control. This demonstrated that CAPRIN-1 proteins are expressed on the cell membrane surface of the human cancer cell lines. The above rate of enhancement in fluorescence intensity was indicated by the rate of increase in mean fluorescence intensity (MFI) in each cell line and calculated according to the following expression:

Rate of increase in mean fluorescence intensity(Rate of enhancement in fluorescence intensity) (%)= ((MFI of cells reacted with the anti-CAPRIN-1 antibodies)–(Control MFI))/(Control MFI)×100.

Also, the fluorescence intensity was measured in 2 kidney cancer cell lines (Caki-1 and Caki-2), a bladder cancer cell line (T24), an ovary cancer cell line (SKOV3), 2 lung cancer cell lines (QG56 and A549), a prostate cancer cell line (PC3), a uterine cervix cancer cell line (SW756), a fibrosarcoma cell line (HT1080), 2 brain tumor cell lines (T98G and U87MG), a gastric cancer cell line (MNK28), 3 colorectal cancer cell lines (Lovo, DLD-1, and HCT-116), and 4 pancreatic cancer cell lines (Capan-2, MIAPaCa-2, Panc-1, and BxPC-3) using the same approach as above. As a result, all the cancer cells had fluorescence intensity at least 35% stronger than that of the control.

As with the results obtained above, CAPRIN-1 protein expression on cancer cell membrane surface was also confirmed using the anti-CAPRIN-1 antibody #1 obtained in Example 2.

Example 5

Preparation of Human-Mouse Chimeric Monoclonal Antibody

The gene amplification fragment comprising the gene of the heavy chain variable region of the anti-CAPRIN-1 antibody #1 obtained in Example 2 was treated at both ends with restriction enzymes, then purified, and inserted according to a routine method into a pcDNA4/myc-His (manufactured by Invitrogen Corp.) vector already having gene inserts of a mouse antibody-derived leader sequence and a human IgG$_1$ H chain constant region comprising the amino acid sequence of SEQ ID NO: 6. Also, the gene amplification fragment comprising the gene of the light chain variable region of the anti-CAPRIN-1 antibody #1 was treated at both ends with restriction enzymes, then purified, and inserted according to a routine method into a pcDNA3.1/myc-His (manufactured by Invitrogen Corp.) vector already having gene inserts of a mouse antibody-derived leader sequence and a human IgG$_1$ L chain constant region comprising the amino acid sequence of SEQ ID NO: 7.

Next, the recombinant vector having the gene insert of the heavy chain variable region of the anti-CAPRIN-1 antibody #1 and the recombinant vector having the gene insert of the light chain variable region were introduced into CHO-K1 cells (obtained from Riken Cell Bank). Specifically, $2 \times 10^5$ CHO-K1 cells were cultured in 1 ml of a Ham's F12 medium (manufactured by Invitrogen Corp.) containing 10% FBS per well of a 12-well culture plate, and washed with PBS(−). Then, 1 ml of a fresh Ham's F12 medium containing 10% FBS per well was added thereto. 250 ng each of the vectors lysed in 30 μl of OptiMEM (manufactured by Invitrogen Corp.) was mixed with 30 μl of Polyfect transfection reagent (manufactured by Qiagen N.V.), and this mixture was added to each well. The CHO-K1 cells cotransfected with the recombinant vectors were cultured in a Ham's F12 medium containing 10% FBS supplemented with 200 μg/ml Zeocin (manufactured by Invitrogen Corp.) and 200 μg/ml Geneticin (manufactured by Roche Diagnostics K.K.) and then inoculated to a 96-well plate at a density of 0.5 cells/well to prepare cell lines stably producing any of human-mouse chimeric monoclonal antibody #1 having the variable regions of the anti-CAPRIN-1 antibody #1, obtained in Example 2.

Each prepared cell line was cultured for 5 days in a 150-cm$^2$ flask at a density of $5 \times 10^5$ cells/ml using 30 ml of a serum-free OptiCHO medium (manufactured by Invitrogen Corp.) to obtain culture supernatants containing the human-mouse chimeric monoclonal antibody #1.

Also, cell lines stably producing human-mouse chimeric comparative antibodies 1 to 26 were prepared as comparative samples in the same way as above respectively using the following comparative antibodies: anti-CAPRIN-1 mouse-derived monoclonal antibodies described in WO2010/016526 [a comparative antibody 1 having the heavy chain variable region of SEQ ID NO: 26 (described therein; the same holds true for the description below) and the light chain variable region of SEQ ID NO: 27; a comparative antibody 2 having the heavy chain variable region of SEQ ID NO: 28 and the light chain variable region of SEQ ID NO: 29; a comparative antibody 3 having the heavy chain variable region of SEQ ID NO: 30 and the light chain variable region of SEQ ID NO: 31; a comparative antibody 4 having the heavy chain variable region of SEQ ID NO: 32 and the light chain variable region of SEQ ID NO: 33; a comparative antibody 5 having the heavy chain variable region of SEQ ID NO: 34 and the light chain variable region of SEQ ID NO: 35; a comparative antibody 6 having the heavy chain variable region of SEQ ID NO: 36 and the light chain variable region of SEQ ID NO: 37; a comparative antibody 7 having the heavy chain variable region of SEQ ID NO: 38 and the light chain variable region of SEQ ID NO: 39; a comparative antibody 8 having the heavy chain variable region of SEQ ID NO: 40 and the light chain variable region of SEQ ID NO: 41; a comparative antibody 9 having the heavy chain variable region of SEQ ID NO: 42 and the light chain variable region of SEQ ID NO: 43; a comparative antibody 10 having the heavy chain variable region of SEQ ID NO: 44 and the light chain variable region of SEQ ID NO: 45; and a comparative antibody 11 having the heavy chain variable region of SEQ ID NO: 46 and the light chain variable region of SEQ ID NO: 47], anti-CAPRIN-1 monoclonal antibodies described in WO2011/096517 [a comparative antibody 12 having the heavy chain variable region of SEQ ID NO: 43 (described therein; the same holds true for the description below) and the light chain variable region of SEQ ID NO: 47; and a comparative antibody 13 having the heavy chain variable region of SEQ ID NO: 43 and the light chain variable region of SEQ ID NO:], anti-CAPRIN-1 monoclonal antibodies described in WO2011/096528 [a comparative antibody 14 having the heavy chain variable region of SEQ ID NO: 43 (described therein; the same holds true for the description below) and the light chain variable region of SEQ ID NO: 47; a comparative antibody 15 having the heavy chain variable region of SEQ ID NO: 51 and the light chain variable region of SEQ ID NO: 55; a comparative antibody 16 having the heavy chain variable region of SEQ ID NO: 59 and the light chain variable region of SEQ ID NO: 63; a comparative antibody 17 having the heavy chain variable region of SEQ ID NO: 76 and the light chain variable region of SEQ ID NO: 80; a comparative antibody 18 having the heavy chain variable region of SEQ ID NO: 84 and the light chain variable region of SEQ ID NO: 88; and a comparative antibody 19 having the heavy chain variable region of SEQ ID NO: 92 and the light chain variable region of SEQ ID NO: 96], an anti-CAPRIN-1 monoclonal antibody described in WO2011/096519 [a comparative antibody 20 having the heavy chain variable region of SEQ ID NO: 42 (described therein; the same holds true for the description below) and the light chain variable region of SEQ ID NO: 46], anti-CAPRIN-1 monoclonal antibodies described in WO2011/096533 [a comparative antibody 21 having the heavy chain variable region of SEQ ID NO: 43 (the same holds true for the description below) and the light chain variable region of SEQ ID NO: 51; a comparative antibody 22 having the heavy chain variable region of SEQ ID NO: 47 and the light chain variable region of SEQ ID NO: 51; and a comparative antibody 23 having the heavy chain variable region of SEQ ID NO: 63 and the light chain variable region of SEQ ID NO: 67], and anti-CAPRIN-1 monoclonal antibodies described in WO2011/096534 [a comparative antibody 24 having the heavy chain variable region of SEQ ID NO: 43 (described therein; the same holds true for the description below) and the light chain variable region of SEQ ID NO: 47; a comparative antibody 25 having the heavy chain variable region of SEQ ID NO: 43 and the light chain variable region of SEQ ID NO: 51; and a comparative antibody 26 having the heavy chain variable region of SEQ ID NO: 63 and the light chain variable region of SEQ ID NO: 67]. Each prepared cell line was cultured for 5 days in a 150-cm$^2$ flask at a density of $5 \times 10^5$ cells/ml using 30 ml of a serum-free OptiCHO medium (manufactured by Invitrogen Corp.) to obtain culture supernatants containing any of the human-mouse chimeric comparative monoclonal antibodies 1 to 26.

Example 6

Expression of CAPRIN-1 on Surface of Various Cancer Cells Using Anti-CAPRIN-1 Monoclonal Antibody Next, the 8 human breast cancer cell lines (ZR75-1, MCF7, T47D, SK-BR-3, MDA-MB-157, BT-20, MDA-MB-231V, and MRK-nu-1), the 2 kidney cancer cell lines (Caki-1 and Caki-2), the bladder cancer cell line (T24), the ovary cancer cell line (SKOV3), the 2 lung cancer cell lines (QG56 and A549), the prostate cancer cell line (PC3), the uterine cervix cancer cell line (SW756), the fibrosarcoma cell line (HT1080), the 2 brain tumor cell lines (T98G and U87MG), the gastric cancer cell line (MNK28), the 3 colorectal cancer cell lines (Lovo, DLD-1, and HCT-116), and the 4 pancreatic cancer cell lines (Capan-2, MIAPaCa-2, Panc-1, and BxPC-3) confirmed to have CAPRIN-1 gene expression were examined for their expression of CAPRIN-1 proteins on the cell surface using the culture supernatants containing the anti-CAPRIN-1 antibody #1 obtained in Example 2. $10^6$ cells of each cell line were centrifuged in each 1.5-ml microcentrifuge tube. Each culture supernatant (100 µl) containing the antibody was added to the tube and left standing for 1 hour on ice. After washing with PBS, FITC-labeled goat anti-mouse IgG (H+L) antibody (manufactured by Jackson ImmunoResearch Laboratories, Inc.) diluted with PBS containing 0.1% FBS was added thereto and left standing at 4° C. for 30 minutes. After washing with PBS, the fluorescence intensity was measured using FACSCalibur (Becton, Dickinson and Company). The negative control used was cells reacted only with secondary antibodies. As a result, the anti-CAPRIN-1 antibody #1 exhibited reactivity with fluorescence intensity at least 30% stronger than that of the negative control. This demonstrated that CAPRIN-1 proteins are expressed on the cell membrane surface of the human cancer cell lines. The above rate of enhancement in fluorescence intensity was indicated by the rate of increase in mean fluorescence intensity (MFI) in each cell line and calculated according to the following expression:

Rate of increase in mean fluorescence intensity(Rate of enhancement in fluorescence intensity) (%)= ((MFI of cells reacted with the anti-CAPRIN-1 antibodies)−(Control MFI))/(Control MFI)×100.

Example 7

Antitumor Activity Against Cancer Cell of Antibody Against CAPRIN-1-Derived Peptide (SEQ ID NO: 5)

In order to evaluate each antibody against the CAPRIN-1-derived peptide (SEQ ID NO: 5) for the strength of its cytotoxicity against cancer cells expressing CAPRIN-1, ADCC activity was determined. The polyclonal antibodies against the peptide (SEQ ID NO: 5) prepared in Example 3 were used in this evaluation. Similar evaluation was conducted using polyclonal antibodies against other human CAPRIN-1-derived peptides (polyclonal antibodies against amino acid residue numbers 50 to 98 in the amino acid sequence of SEQ ID NO: 2 of human CAPRIN-1 and polyclonal antibodies against amino acid residue numbers 233 to 305, which were prepared in Example 3) as antibodies to be compared and the rabbit serum-derived control antibodies prepared in Example 3 as a negative control.

$10^6$ cells each of the human breast cancer cell line MDA-MB-231V, the human colorectal cancer cell line DLD-1, the human pancreatic cancer cell line Capan-2, and the human lung cancer cell line QG56 confirmed to have CAPRIN-1 expression were collected into a 50-ml centrifuge tube, to which 100 µCi of chromium 51 was then added, followed by incubation at 37° C. for 2 hours. Then, the cells were washed three times with an RPMI1640 medium containing 10% fetal calf serum and added at a density of $2 \times 10^3$ cells/well to each 96-well V-bottom plate. The polyclonal antibodies against the human CAPRIN-1-derived peptide (SEQ ID NO: 5) and two types of polyclonal antibodies against other human CAPRIN-1-derived peptides (polyclonal antibodies against amino acid residue numbers 50 to 98 in SEQ ID NO: 2 of human CAPRIN-1 and polyclonal antibodies against amino acid residue numbers 233 to 305) as described above were separately added thereto at a concentration of 1 μg/well. Lymphocytes separated from human peripheral blood according to a routine method were further added thereto at a density of $4 \times 10^5$ cells/well and cultured at 37° C. for 4 hours under conditions of 5% $CO_2$. After the culture, the amount of chromium (Cr) 51 released from damaged cancer cells was measured in the culture supernatant to calculate the ADCC activity against the cancer cells of the polyclonal antibodies against each human CAPRIN-1-derived peptide. As a result, all the polyclonal antibodies obtained by immunization with the partial peptides of human CAPRIN-1 having an amino acid sequence of amino acid residue numbers 50 to 98 or amino acid residue numbers 233 to 305 of SEQ ID NO: 2 of human CAPRIN-1 had activity less than 8% against the human breast cancer cell line MDA-MB-231V, the human colorectal cancer cell line DLD-1, the human pancreatic cancer cell line Capan-2, and the human lung cancer cell line QG56. By contrast, the groups supplemented with the polyclonal antibodies against the human CAPRIN-1-derived peptide (SEQ ID NO: 5) were confirmed to have 27% or higher cytotoxic activity against all the cancer cell lines. The negative control antibodies had activity less than 5% against all the cancer cells. These results demonstrated that the antibody against CAPRIN-1 shown in SEQ ID NO: 5 exerts strong cytotoxic activity against cancer cells expressing CAPRIN-1.

These results about cytotoxic activity were obtained by: mixing the antibody against CAPRIN-1 used in the present invention, lymphocytes, and $2 \times 10^3$ cells of each cancer cell line with incorporated chromium 51, as described above: culturing the cells for 4 hours; after the culture, measuring the amount of chromium 51 released into the medium; and calculating the cytotoxic activity against each cancer cell line according to the following expression*:

>    *Expression: Cytotoxic activity (%)=Amount of chromium 51 released from the target cells supplemented with the antibody against CAPRIN-1 and lymphocytes/Amount of chromium 51 released from target cells supplemented with 1 N hydrochloric acid×100.

The human-mouse chimeric monoclonal antibody obtained in Example 5 were evaluated for their cytotoxic activity against human cancer cells. The culture supernatant of each cell line producing any of the antibodies was purified using Hitrap Protein A Sepharose FF (manufactured by GE Healthcare Bio-Sciences Ltd.). After replacement with PBS (−), the solution was filtered through a 0.22-μm filter (manufactured by Millipore Corp.). The resulting antibody was used for activity assay. $10^6$ cells each of the human breast cancer cell line MDA-MB-231V, the human colorectal cancer cell line DLD-1, the human pancreatic cancer cell line Capan-2, and the human lung cancer cell line QG56 were collected into a 50-ml centrifuge tube, to which 100 μCi of chromium 51 was then added, followed by incubation at 37° C. for 2 hours. Then, the cells were washed three times with an RPMI1640 medium containing 10% FBS and added at a density of $2 \times 10^3$ cells/well to each 96-well V-bottom plate to prepare target cells. The purified antibodies (human-mouse chimeric anti-CAPRIN-1 antibody #1) and the human-mouse chimeric comparative monoclonal antibodies 1 to 26 obtained in Example 5 were each added thereto at a concentration of 0.75 μg/well. A cell population containing human NK cells was separated using a routine method from human peripheral blood lymphocytes prepared according to a routine method. The cell population containing human NK cells that was used in this evaluation was prepared as follows: human peripheral blood mononuclear cells separated using a specific gravity separation solution Histopaque for peripheral blood mononuclear cell separation (Sigma-Aldrich Corp.) were reacted with FITC fluorescent dye-labeled antibodies (anti-human CD3 antibody, anti-human CD20 antibody, anti-human CD19 antibody, anti-human CD11c antibody, or anti-HLA-DR antibody (Becton, and Dickinson and Company)), and a cell population containing NK cells unstained with the antibodies was separated using a cell sorter (FACS Vantage SE (Becton, and Dickinson and Company)) or human NK cell separation kit (manufactured by Miltenyi Biotec K.K.). The separated cell population containing NK cells was added to the plate at a density of $2 \times 10^5$ cells/well and cultured at 37° C. for 4 hours under conditions of 5% $CO_2$. After the culture, the amount of chromium 51 released from damaged tumor cells was measured in the culture supernatant to calculate the cytotoxic activity of each anti-CAPRIN-1 antibody against the cancer cells. The negative control used was cells supplemented with isotype control antibodies. As a result, the isotype control antibodies used had cytotoxic activity of less than 5% against all of the cancer cell lines, and the human-mouse chimeric comparative monoclonal antibodies 1 to 26 used had cytotoxic activity of less than 5% against MDA-MB-231V, less than 8% against DLD-1, less than 10% against Capan-2, and less than 10% against QG56. By contrast, the human-mouse chimeric anti-CAPRIN-1 antibody #1 had cytotoxic activity of 12% or higher against MDA-MB-231V, 22% or higher against DLD-1, 28% or higher against Capan-2, and 21% or higher against QG56. Likewise, the isotype control antibodies used and the comparative antibodies 1 to 26 used had cytotoxic activity less than 4% against all of other cancer cells, breast cancer cell lines T47D, Hs578T, BT-20, SK-BR-3, MCF7, and MRK-nu-1, a glioma cell line T98G, a lung cancer cell line A549, a kidney cancer cell line Caki-1, a uterine cervix cancer cell line SW756, a bladder cancer cell line T24, a gastric cancer cell line MKN28, a colorectal cancer cell line SW480, a leukemia cell line AML5, and a lymphoma cell line Ramos. By contrast, the human-mouse chimeric monoclonal antibody was confirmed to have 10% or higher cytotoxic activity against these cell lines. These results showed that the antibodies against the CAPRIN-1-derived peptide shown in SEQ ID NO: 5 damage CAPRIN-1-expressing cancer cells through their ADCC activity, and demonstrated that the human-mouse chimeric anti-CAPRIN-1 antibody #1 exhibits stronger cytotoxic activity against human cancer cells than that of the comparative antibodies 1 to 26.

These results about cytotoxic activity were obtained by: mixing the antibody against CAPRIN-1 used in the present invention, lymphocytes (cell population containing NK cells), and $2 \times 10^3$ cells of each cancer cell line with incorporated chromium 51, as described above: culturing the cells for 4 hours; after the culture, measuring the amount of chromium 51 released into the medium; and calculating the cytotoxic activity against each cancer cell line according to the following expression*:

>    *Expression: Cytotoxic activity (%)=Amount of chromium 51 released from the target cells supplemented with the antibody against CAPRIN-1 and lymphocytes(cell population containing NK cells)/Amount of chromium 51 released from target cells supplemented with 1 N hydrochloric acid×100.

Example 8

The Number of CAPRIN-1 Molecules on Surface of Various Cancer Cells Recognized by Anti-CAPRIN-1 Antibody #1

A human breast cancer cell line (MDA-MB-231V), a kidney cancer cell line (Caki-1), a bladder cancer cell line (T24), an ovary cancer cell line (SKOV3), lung cancer cell lines (QG56 and A549), a pancreatic cancer cell line (Capan-2), a prostate cancer cell line (PC3), a uterine cervix cancer cell line (SW756), a fibrosarcoma cell line (HT1080), a brain tumor cell line (T98G), a gastric cancer cell line (MKN28), colorectal cancer cell lines (Lovo and DLD-1), a leukemia cell line (AML5), and a lymphoma cell line (Ramos) were examined using an assay kit "QIFIKIT" for the number of molecules (manufactured by Dako Japan Inc.) for the number of CAPRIN-1 molecules on their cell surface recognized by the anti-CAPRIN-1 antibody #1. Similarly, the number of CAPRIN-1 molecules on the surface of these various cancer cells was also examined using the anti-CAPRIN-1 comparative monoclonal antibodies 1 to 26 prepared in Example 5.

According to the protocol attached to the kit, each antibody (anti-CAPRIN-1 antibodies #1 and comparative antibodies 1 to 26) was diluted into 5 μg/ml (in terms of final concentration) with PBS, and this dilution was added to each cell line and reacted for 30 minutes. After washing with PBS, fluorescently labeled anti-mouse IgG antibodies attached to the kit were added as secondary antibodies, together with calibration beads attached to the kit, to each cell line and left standing for 45 minutes on ice. Each cell line and the calibration beads were washed with PBS. Then, the fluorescence intensity was measured using FACSCalibur (Becton, Dickinson and Company) to obtain a mean fluorescence intensity value (mean). Also, a mean fluorescence intensity value (mean) was obtained by the same assay as above for the comparative antibodies. The negative control used was cells reacted with isotype control antibodies, and a mean was also obtained. Each mean fluorescence intensity value (mean) was used to calculate the number of molecules according to the protocol attached to the kit. As a result, the number of CAPRIN-1 molecules on the surface of various cancer cells recognized by the anti-CAPRIN-1 monoclonal antibody and the comparative antibodies 12 to 26 was $10^5$ or more per cell for all the examined human cancer cell lines. On the other hand, the number of molecules recognized by the comparative antibodies 1 to 11 was less than $10^5$ per cell.

INDUSTRIAL APPLICABILITY

The antibody of the present invention is useful for the treatment and/or prevention of cancer.

All publications, patents, and patent applications cited herein are incorporated herein by reference in their entirety.

The invention claimed is:

1. An antibody or a fragment thereof which has immunological reactivity with a partial CAPRIN-1 polypeptide consisting of the amino acid sequence of SEQ ID NO: 5.

2. The antibody or fragment thereof according to claim 1, wherein the antibody or fragment thereof has cytotoxic activity against a cancer cell expressing a CAPRIN-1 protein.

3. The antibody or fragment thereof according to claim 1, wherein the antibody is a monoclonal antibody or a polyclonal antibody.

4. The antibody or fragment thereof according to claim 1, wherein the antibody is a human antibody, a humanized antibody, a chimeric antibody, a single-chain antibody, or a multispecific antibody.

5. The antibody or fragment thereof according to claim 1, wherein the antibody or fragment thereof comprises a heavy chain variable region comprising complementarity determining regions of SEQ ID NOs: 8, 9, and 10 (CDR1, CDR2, and CDR3, respectively) and a light chain variable region comprising complementarity determining regions of SEQ ID NOs: 12, 13, and 14 (CDR1, CDR2, and CDR3, respectively) and has immunological reactivity with the CAPRIN-1 protein.

6. The antibody or fragment thereof according to claim 1, wherein the antibody or fragment thereof is conjugated with an antitumor agent.

7. A pharmaceutical composition for treatment of a caprin-1 expressing cancer, comprising an antibody or fragment thereof according to claim 1 as an active ingredient.

8. The pharmaceutical composition according to claim 7, wherein the cancer is breast cancer, kidney cancer, pancreatic cancer, colorectal cancer, lung cancer, brain tumor, gastric cancer, uterine cervix cancer, ovary cancer, prostate cancer, bladder cancer, esophageal cancer, leukemia, lymphoma, fibrosarcoma, mastocytoma, or melanoma.

9. A combination drug for treatment of a caprin-1 expressing cancer, comprising a pharmaceutical composition according to claim 7 and a pharmaceutical composition comprising an antitumor agent.

10. A DNA encoding an antibody or fragment thereof according to claim 1.

11. A method for treatment of a caprin-1 expressing cancer, comprising administering an antibody or fragment thereof according to claim 1 to a subject.

12. The antibody or fragment thereof according to claim 2, wherein the antibody is a monoclonal antibody or a polyclonal antibody.

13. The antibody or fragment thereof according to claim 2, wherein the antibody is a human antibody, a humanized antibody, a chimeric antibody, a single-chain antibody, or a multispecific antibody.

14. The antibody or fragment thereof according to claim 3, wherein the antibody is a human antibody, a humanized antibody, a chimeric antibody, a single-chain antibody, or a multispecific antibody.

15. The antibody or fragment thereof according to claim 2, wherein the antibody or fragment thereof comprises a heavy chain variable region comprising complementarity determining regions of SEQ ID NOs: 8, 9, and 10 (CDR1, CDR2, and CDR3, respectively) and a light chain variable region comprising complementarity determining regions of SEQ ID NOs: 12, 13, and 14 (CDR1, CDR2, and CDR3, respectively) and has immunological reactivity with the CAPRIN-1 protein.

16. The antibody or fragment thereof according to claim 3, wherein the antibody or fragment thereof comprises a heavy chain variable region comprising complementarity determining regions of SEQ ID NOs: 8, 9, and 10 (CDR1, CDR2, and CDR3, respectively) and a light chain variable region comprising complementarity determining regions of SEQ ID NOs: 12, 13, and 14 (CDR1, CDR2, and CDR3, respectively) and has immunological reactivity with the CAPRIN-1 protein.

17. The antibody or fragment thereof according to claim 4, wherein the antibody or fragment thereof comprises a heavy chain variable region comprising complementarity determining regions of SEQ ID NOs: 8, 9, and 10 (CDR1, CDR2, and CDR3, respectively) and a light chain variable region comprising complementarity determining regions of SEQ ID NOs: 12, 13, and 14 (CDR1, CDR2, and CDR3, respectively) and has immunological reactivity with the CAPRIN-1 protein.

18. The antibody or fragment thereof according to claim 2, wherein the antibody or fragment thereof is conjugated with an antitumor agent.

19. The antibody or fragment thereof according to claim 3, wherein the antibody or fragment thereof is conjugated with an antitumor agent.

20. The antibody or fragment thereof according to claim 4, wherein the antibody or fragment thereof is conjugated with an antitumor agent.

\* \* \* \* \*